United States Patent
Strongin et al.

(10) Patent No.: US 12,358,923 B2
(45) Date of Patent: Jul. 15, 2025

(54) SEMINAPHTHOFLUOROPHORE-SELENIUM PROBES FOR THIOREDOXIN REDUCTASE

(71) Applicant: Portland State University, Portland, OR (US)

(72) Inventors: Robert M. Strongin, Portland, OR (US); Jorge O. Escobedo Cordova, Portland, OR (US); Tendai Mafireyi, Portland, OR (US)

(73) Assignee: Portland State University, Portland, OR (US)

( * ) Notice: Subject to any disclaimer, the term of this patent is extended or adjusted under 35 U.S.C. 154(b) by 722 days.

(21) Appl. No.: 17/762,348

(22) PCT Filed: Sep. 24, 2020

(86) PCT No.: PCT/US2020/052511
§ 371 (c)(1),
(2) Date: Mar. 21, 2022

(87) PCT Pub. No.: WO2021/062000
PCT Pub. Date: Apr. 1, 2021

(65) Prior Publication Data
US 2023/0002803 A1 Jan. 5, 2023

Related U.S. Application Data

(60) Provisional application No. 62/907,177, filed on Sep. 27, 2019.

(51) Int. Cl.
| | | |
|---|---|---|
| C07D 493/10 | (2006.01) | |
| C12Q 1/26 | (2006.01) | |
| G01N 21/29 | (2006.01) | |
| G01N 21/64 | (2006.01) | |
| G01N 21/78 | (2006.01) | |

(52) U.S. Cl.
CPC ............ C07D 493/10 (2013.01); C12Q 1/26 (2013.01); C12Y 108/01009 (2013.01); G01N 21/29 (2013.01); G01N 21/6428 (2013.01); G01N 21/78 (2013.01)

(58) Field of Classification Search
None
See application file for complete search history.

(56) References Cited

FOREIGN PATENT DOCUMENTS

CN 104 974 744 A 10/2015

OTHER PUBLICATIONS

Manjare et al., "Selenium- and Tellurium-Containing Fluorescent Molecular Probes for the Detection of Biologically Important Analytes", Accounts of Chemical Research, vol. 47, pp. 2985-2998 (Year: 2014).*
Chuard, et al., "Diselenolane-mediated cellular uptake," *Chem. Sci.*, Jan. 17, 2018, 9:1860-1866.
Fernandez-Lodeiro, et al., "Synthesis and Biological Properties of Selenium- and Tellurium-containing dyes," *Dyes and Pigments*, Nov. 2014, 110:28-48, doi: 10.1016/j.dyepig.2014.04.044 (accepted manuscript, 87 pages).
International Search Report and Written Opinion dated Jan. 5, 2021 issued on corresponding International Application No. PCT/US2020/052511, 7 pages.
Liu, et al., "A small molecule probe reveals declined mitochondrial thioredoxin reductase activity in a Parkinson's disease model," *Chem. Commun.*, Feb. 7, 2016, 52:2296-2299.
Lou, et al., "A fluorescent probe for rapid detection of thiols and imaging of thiols reducing repair and H2O2 oxidative stress cycles in living cells," *Chem. Commun.*, Jan. 14, 2013, 49:391-393.
Mafireyi, et al., "A Diselenide Turn-on Fluorescent Probe for the Detection of Thioredoxin Reductase," *Angew, Chem. Int. Ed.*, May 24, 2020, 59:15147-15151.
Extended European Search Report and Written Opinion, dated Sep. 19, 2023, issued in corresponding EPC Application No. 20867137.0, 9 pages.

* cited by examiner

*Primary Examiner* — Michelle F. Paguio Frising
(74) *Attorney, Agent, or Firm* — Klarquist Sparkman, LLP

(57) ABSTRACT

Seminaphthofluorophore-selenium probes are disclosed. The probes include a seminaphthofluorophore scaffold substituted with at least one diselenide moiety having a formula —Y—C(Q)O—(CH$_2$)$_m$—Se—Se—(CH$_2$)$_n$—OR$^f$, where R$^f$ is hydrogen or C$_1$-C$_3$ alkyl, Q is O or S, Y is O or N(R$^g$) where R$^g$ is H or alkyl, and m and n independently are integers. The probes may be used to detect presence of a thioredoxin reductase.

20 Claims, 3 Drawing Sheets

SEMINAPHTHOFLUOROPHORE-SELENIUM PROBES FOR THIOREDOXIN REDUCTASE

CROSS REFERENCE TO RELATED APPLICATION

This is the U.S. National Stage of International Application No. PCT/US2020/052511, filed Sep. 24, 2020, which was published in English under PCT Article 21(2), which in turn claims the benefit of the earlier filing date of U.S. Provisional Application No. 62/907,177, filed Sep. 27, 2019, which is incorporated by reference herein in its entirety.

FIELD

This disclosure concerns embodiments of seminaphthofluorophore-selenium probes, as well as methods of using the probes to detect a thioredoxin reductase.

BACKGROUND

Thioredoxin reductase enzymes in mammals are a group of selenoproteins that exist in three main isoforms; in the cytosol as TrxR1, in mitochondria as TrxR2 and a third form, thioredoxin-glutathione reductase (TGR) mainly expressed in the testis. The incorporation of a selenocysteine (Sec) residue at the C-terminal active sites of mammalian thioredoxin reductases gives the enzyme broader substrate specificity compared to the prokaryotic and invertebrate enzymes that utilize cysteine. Sec has a $pK_a \approx 5.2$, whereas Cys residues have a $pK_a \approx 8.5$. Therefore, the selenol residue in mammalian TrxRs is deprotonated at physiological pH, making TrxRs highly reactive.

The cytosolic thioredoxin reductase system comprises TrxR1, thioredoxin (Trx) and NADPH. NADPH is the electron donor for TrxR1, which reduces the Trx disulfide bonds. Trx participates in both the metabolism of reactive oxygen species, and in redox signaling in cells, often by providing reducing equivalents to another class of protein oxidoreductases, the peroxiredoxins. TrxR1 is overexpressed in many cancers, aiding their growth and proliferation and also inhibiting apoptosis. TrxR1 levels have been shown to directly correlate with the progression of melanoma, human lung carcinoma and prostate cancer.

SUMMARY

This disclosure concerns seminaphthofluorophore-selenium probes and methods of using the probes. In some embodiments, the seminaphthofluorophore-selenium probe is a compound according to Formula I, or an ionized form or salt thereof:

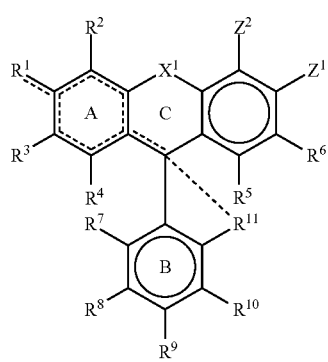

(I)

where each bond depicted as "⸺" is a single or double bond as needed to satisfy valence requirements; $Z^1$ and $Z^2$ independently are hydrogen, hydroxyl, or thiol, or $Z^1$ and $Z^2$ together with the atoms to which they are attached form a substituted or unsubstituted 6-membered ring; $X^1$ is O, S, Se, $Si(R^a)(R^b)$, $Ge(R^a)(R^b)$, $Sn(R^a)(R^b)_2$, $C(R^a)(R^b)_2$, or $NR^b$ where $R^a$ is H or $C_1$-$C_{10}$ alkyl and $R^b$ is H, $C_1$-$C_{10}$ alkyl, —COOH, or —COOR$^c$ where $R^c$ is $C_1$-$C_{10}$ alkyl or a conjugatable moiety; $R^1$ is hydrogen, hydroxyl, halogen, thiol, amino, alkyl amino, oxygen, sulfur, imino, iminium, alkyl imino, alkyl iminium, cycloalkyl imino, or a diselenide moiety, and $R^2$ and $R^3$ independently are hydrogen, hydroxy, thiol, $C_1$-$C_{10}$ alkyl, carboxyalkyl, amino, alkoxy, or halogen, or $R^1$-$R^3$ together with Ring A form a tricyclic ring system with a nitrogen at $R^1$ and a single bond between $R^1$ and ring A; $R^4$-$R^6$ independently are hydrogen, hydroxy, thiol, $C_1$-$C_{10}$ alkyl, carboxyalkyl, amino, alkoxy, or halogen; $R^7$, $R^8$, and $R^{10}$ independently are hydrogen, alkyl, acyl, carboxyl, nitro, amino, alkyl amino, —SO$_3$H, —COOH, or —COOR$^d$ where $R^d$ is $C_1$-$C_{10}$ alkyl or a conjugatable moiety; $R^9$ is hydrogen, alkyl, acyl, carboxyl, nitro, amino, alkyl amino, —SO$_3$H, a diselenide moiety, —COOH, or —COOR$^d$ where $R^d$ is $C_1$-$C_{10}$ alkyl or a conjugatable moiety; and $R^{11}$ is one or more atoms forming a ring system with rings C and B and the bond depicted as "⸺" in ring C is a single bond, or $R^{11}$ is —COOH, —COO$^-$ or —COOR$^e$ where $R^e$ is $C_1$-$C_{10}$ alkyl or a counter ion with a net single positive charge and the bond depicted as "⸺" in ring C is a double bond, wherein the compound comprises at least one diselenide moiety, and each diselenide moiety independently has a formula —Y—C(Q)O—(CH$_2$)$_m$—Se—Se—(CH$_2$)$_n$—OR$^f$, where R$^f$ is hydrogen or $C_1$-$C_3$ alkyl, Q is O or S, Y is O or N(R$^g$) where R$^g$ is H or alkyl, and m and n independently are integers from 1-5.

In one embodiment, $Z^1$ is hydroxyl or thiol, $Z^2$ is hydrogen, $R^1$ is hydroxyl or thiol, and $R^9$ is —Y—C(Q)O—(CH$_2$)$_m$—Se—Se—(CH$_2$)$_n$—OR$^f$.

In some embodiments, $Z^1$ and $Z^2$ together with the atoms to which they are attached form a substituted or unsubstituted 6-membered ring and the compound has a structure according to Formula II, or an ionized form or salt thereof:

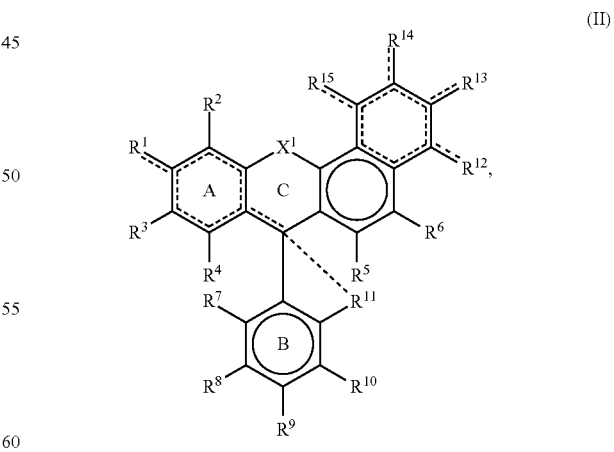

(II)

wherein $R^{12}$-$R^{14}$ independently are hydrogen, halogen, hydroxy, oxygen, thiol, amino, alkyl amino, alkoxy, sulfur, imino, iminium, alkyl imino, or alkyl iminium; and $R^{15}$ is hydrogen, halogen, hydroxy, oxygen, thiol, amino, alkyl amino, alkoxy, sulfur, imino, iminium, alkyl imino, or alkyl iminium, or a diselenide moiety. In one embodiment, $R^1$ is —Y—C(Q)O—$(CH_2)_m$—Se—Se—$(CH_2)_n$—$OR^f$, and $R^{15}$ is $C_1$-$C_3$ alkoxy or hydroxy. In an independent embodiment, $R^1$ is O or alkyl iminium, and $R^{15}$ is —Y—C(Q)O—$(CH_2)_m$—Se—Se—$(CH_2)_n$—$OR^f$. In another independent embodiment, both $R^1$ and $R^{15}$ independently are —Y—C(Q)O—$(CH_2)_m$—Se—Se—$(CH_2)_n$—$OR^f$.

Embodiments of a method for determining presence of a thioredoxin reductase include combining a compound as disclosed herein with a biological sample comprising, or suspected of comprising, a thioredoxin reductase; allowing a reaction between the biological sample and the compound to proceed for an effective period of time to produce a detectable change in the compound's color or emission spectrum, where the detectable change indicates that the thioredoxin reductase is present in the biological sample; and detecting the change. In some embodiments, detecting the change comprises detecting a visible color change or detecting an increase in fluorescence intensity at a wavelength within a range of 570-590 nm after the effective period of time. In any of the foregoing embodiments, the biological sample may comprise a tissue sample. The biological sample may include cancer cells (e.g., melanoma cells, lung carcinoma cells, prostate cancer cells) or neurological tissue.

The foregoing and other objects, features, and advantages of the invention will become more apparent from the following detailed description, which proceeds with reference to the accompanying figures.

DETAILED DESCRIPTION

Figure 1:
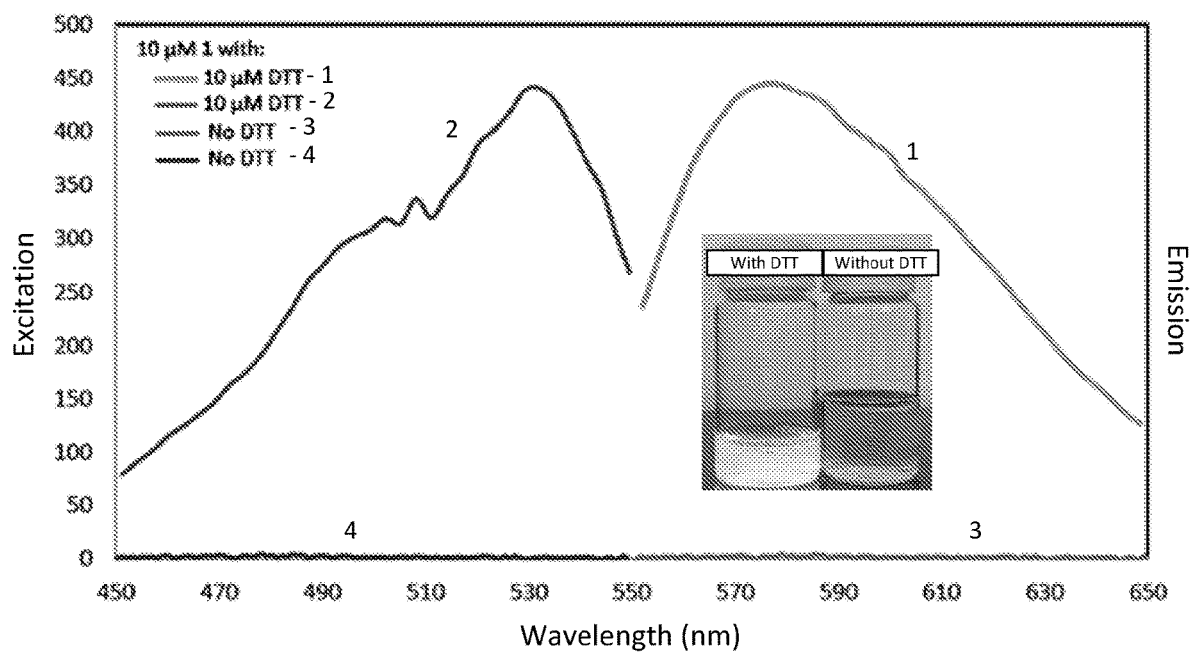
FIG. 1 is a graph illustrating excitation and emission spectra for an exemplary probe as disclosed herein before and after reduction with dithiothreitol.

This disclosure concerns seminaphthofluorophore-selenium probes. In some embodiments, the compounds are used to detect presence of a thioredoxin reductase. Advantageously, some embodiments of the disclosed compounds selectively detect thioredoxin reductases and do not react to a measurable extent with other biological thiols (e.g., cysteine, homocysteine, glutathione) or sulfur-containing ions (e.g., sulfide, sulfite, sulfate, thiosulfate).

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0). The presently disclosed compounds also include all isotopes of atoms present in the compounds, which can include, but are not limited to, deuterium, tritium, $^{18}F$, $^{14}C$, etc.

In order to facilitate review of the various embodiments of the disclosure, the following explanations of specific terms are provided:

Acyl: An organic functional group having the general formula —C(O)R, where R is hydrogen, alkyl, heteroalkyl, haloalkyl, aliphatic, heteroaliphatic, aryl, or heteroaryl.

Alkoxy: An organic functional group having the general formula —OR, where R is a substituted or unsubstituted alkyl or a substituted or unsubstituted cycloalkyl group. In certain examples R is a $C_{1-6}$ alkyl group or a $C_{3-6}$ cycloalkyl group. Methoxy (—$OCH_3$) and ethoxy (—$OCH_2CH_3$) are exemplary alkoxy groups. In a substituted alkoxy, R is substituted alkyl or substituted cycloalkyl, examples of which include haloalkoxy groups, such as —$OCF_2H$, or —$OCF_3$.

Alkyl: A hydrocarbon group having a saturated carbon chain. The chain may be cyclic, branched or unbranched. Examples, without limitation, of alkyl groups include methyl, ethyl, propyl, butyl, pentyl, hexyl, heptyl, octyl, nonyl and decyl.

Amino: A functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —$NH_2$. "Monosubstituted amino" means a radical —N(H)R substituted as above and includes, e.g., methylamino, (1-methylethyl) amino, phenylamino, and the like. "Di-substituted amino" means a radical —N(R)R' substituted as above and includes, e.g., dimethylamino, methylethylamino, di(1-methylethyl) amino, and the like. When at least one of R and R' is alkyl, the group may be referred to as an alkyl amino group. When at least one of R and R' is cycloalkyl, the group may be referred to as a cycloalkyl amino group.

Carboxyalkyl: A functional group with the formula —COOR where R is alkyl.

Carboxyl: A —COOH radical. Substituted carboxyl refers to —COOR where R is aliphatic, heteroaliphatic, alkyl, heteroalkyl, or a carboxylic acid or ester.

Conjugatable moiety: A portion of a molecule that allows the molecule to be conjugated (i.e., coupled or bound) to another molecule, e.g., to a drug or targeting agent such as an antibody.

Conjugate: Two or more moieties directly or indirectly coupled together. For example, a first moiety may be covalently or noncovalently (e.g., electrostatically) coupled to a second moiety. Indirect attachment is possible, such as by using a "linker" (a molecule or group of atoms positioned between two moieties). Exemplary conjugates include, but are not limited to, probe-targeting agent conjugates, such as probe-antibody conjugates.

Contacting: Placement that allows association between two or more moieties or substances, particularly direct physical association, for example both in solid form and/or in liquid form (for example, the placement of a biological sample, such as a biological sample affixed to a slide, in contact with a compound or composition, such as a solution containing a compound as disclosed herein).

Counter ion: The ion, or ions, accompanying another ionic species to provide electric neutrality.

Detect: To determine if an agent (such as an enzyme) is present or absent, for example, in a sample. In some examples, this can further include quantification. "Detecting" refers to any method of determining if something exists, or does not exist, such as determining if a target molecule is present in a biological sample. For example, "detecting" can include using a visual or a mechanical device to determine if a sample displays a specific characteristic. Some embodiments of the disclosed compounds undergo a change in color, absorbance spectrum, and/or emission spectrum when a diselenide moiety of the compound is cleaved, e.g., by a thioredoxin reductase.

Iminium: A functional group having the formula $>C=N^+(R)(R')$ where R and R' independently are H or alkyl. When at least one of R and R' is alkyl, the group may be referred to as an alkyl iminium group. When at least one of R and R' is cycloalkyl, the group may be referred to as a cycloalkyl iminium group.

Imino: A functional group having the formula $>C=NR$ where R is H or an alkyl group. When R is alkyl, the group may be referred to as an alkyl imino group. When R is cycloalkyl, the group may be referred to as a cycloalkyl imino group.

Moiety: A moiety is a fragment of a molecule, or a portion of a conjugate.

NADPH: the reduced form of $NADP^+$ (nicotinamide adenine dinucleotide reductase).

Nitro: A functional group —$NO_2$.

Subject: An animal (human or non-human) subjected to a treatment, observation or experiment.

Target: An intended molecule to which a disclosed cyanine fluorophore comprising a targeting agent is capable of specifically binding. Examples of targets include proteins and nucleic acid sequences present in tissue samples. A target area is an area in which a target molecule is located or potentially located.

Targeting agent: An agent that promotes preferential or targeted delivery to a target site, for example, a targeted location in a subject's body, such as a specific organ, organelle, physiologic system, tissue, or site of pathology such as a tumor, area of infection, or area of tissue injury. Targeting agents function by a variety of mechanisms, such as selective concentration in a target site or by binding to a specific binding partner. Suitable targeting agents include, but are not limited to, proteins, polypeptides, peptides, glycoproteins and other glycoslyated molecules, oligonucleotides, phospholipids, lipoproteins, alkaloids, and steroids. Exemplary targeting agents include antibodies, antibody fragments, affibodies, aptamers, albumin, cytokines, lymphokines, growth factors, hormones, enzymes, immune modulators, receptor proteins, antisense oligonucleotides, avidin, nano particles, and the like. Particularly useful of targeting agents are antibodies, nucleic acid sequences, and receptor ligands, although any pair of specific binding partners can be readily employed for this purpose.

Thiol: A functional group —SH.

Thioredoxin: A class of small (~12 kDa) redox proteins present in nearly all living organisms. Thioredoxins include a cysteine in the active site, typically as Cys-Gly-Pro-Cys.

TrxR: thioredoxin reductase

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazolyl and pyridinyl rings, atropisomers are also possible and are also specifically included in the compounds of the invention.

In any embodiments, any or all hydrogens present in the compound, or in a particular group or moiety within the compound, may be replaced by a deuterium or a tritium.

Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

II. SEMINAPHTHOFLUOROPHORE-SELENIUM PROBES

The disclosed seminaphthofluorophore-selenium probes include a seminaphthofluorophore scaffold and at least one diselenide moiety. In some embodiments, the probe is a compound according to Formula I, or an ionized form or salt thereof:

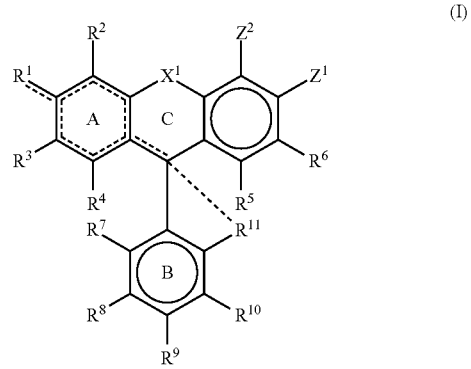

(I)

where each bond depicted as "------" is a single or double bond as needed to satisfy valence requirements.

With respect to Formula I, $Z^1$ and $Z^2$ independently are hydrogen, hydroxyl, or thiol, or $Z^1$ and $Z^2$ together with the atoms to which they are attached form a substituted or unsubstituted 6-membered ring. $X^1$ is O, S, Se, $Si(R^a)(R^b)$, $Ge(R^a)(R^b)$, $Sn(R^a)(R^b)_2$, $C(R^a)(R^b)_2$, or $NR^b$ where $R^a$ is H or $C_1$-$C_{10}$ alkyl and $R^b$ is H, $C_1$-$C_{10}$ alkyl, —COOH, or —$COOR^c$ where $R^c$ is $C_1$-$C_{10}$ alkyl or a conjugatable moiety. $R^1$ is hydrogen, hydroxyl, halogen, thiol, amino, alkyl amino, oxygen, sulfur, imino, iminium, alkyl imino, alkyl iminium, cycloalkyl imino, or a diselenide moiety; and $R^2$ and $R^3$ independently are hydrogen, hydroxy, thiol, $C_1$-$C_{10}$ alkyl, carboxyalkyl, amino, alkoxy, or halogen, or $R^1$-$R^3$ together with Ring A form a tricyclic ring with a nitrogen at $R^1$ and a single bond between $R^1$ and ring A. $R^2$ and $R^3$ independently are hydrogen, hydroxy, thiol, $C_1$-$C_{10}$ alkyl, carboxyalkyl, amino, alkoxy, or halogen, or $R^1$-$R^3$ together with Ring A form a tricyclic ring with a nitrogen at $R^1$ and the bond between $R^1$ and ring A is a single bond. $R^4$-$R^6$ independently are hydrogen, hydroxy, thiol, $C_1$-$C_{10}$ alkyl, carboxyalkyl, amino, alkoxy, or halogen. $R^7$, $R^8$, and $R^{10}$ independently are hydrogen, alkyl, acyl, carboxyl, nitro, amino, alkyl amino, —$SO_3H$, —COOH, or —$COOR^d$ where $R^d$ is $C_1$-$C_{10}$ alkyl or a conjugatable moiety. $R^9$ is hydrogen, alkyl, acyl, carboxyl, nitro, amino, alkyl amino, —$SO_3H$, a diselenide moiety, —COOH, or —$COOR^d$ where $R^d$ is $C_1$-$C_{10}$ alkyl or a conjugatable moiety. $R^{11}$ is one or more atoms forming a ring system with rings C and B and the bond depicted as "------" in ring C is a single bond, or $R^{11}$ is —COOH, —$COO^-$ or —$COOR^e$ where $R^e$ is $C_1$-$C_{10}$ alkyl or a counter ion with a net single positive charge and the bond depicted as "------" in ring C is a double bond. The compound comprises at least one diselenide moiety, and each diselenide moiety independently has a formula —Y—C(Q)O—$(CH_2)_m$—Se—Se—$(CH_2)_n$—$OR^f$, where $R^f$ is hydrogen or $C_1$-$C_3$ alkyl, Q is O or S, Y is —O— or —$N(R^g)$— where $R^g$ is H or alkyl, and m and n independently are integers from 1-5.

$Z^1$ and $Z^2$ independently are hydrogen, hydroxyl, or thiol, or $Z^1$ and $Z^2$ together with the atoms to which they are attached form a substituted or unsubstituted 6-membered ring. In one embodiment, $Z^1$ is hydroxyl and $Z^2$ is hydrogen.

In some embodiments, $Z^1$ and $Z^2$ together with the atoms to which they are attached form a substituted or unsubstituted 6-membered ring, and the compound has a structure according to formula II, or an ionized form or salt thereof:

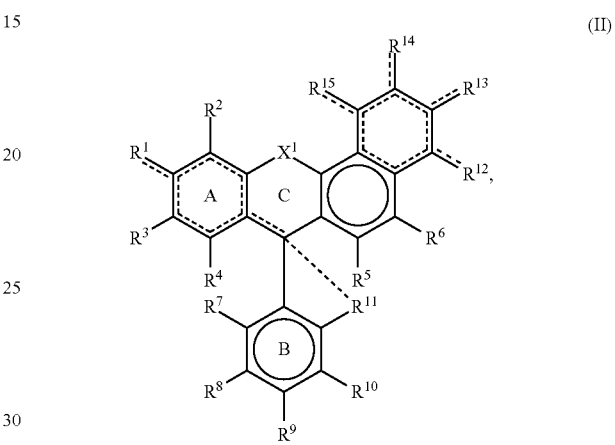

(II)

With respect to Formula II, $X^1$ and $R^1$-$R^{11}$ are as previously defined. $R^{12}$-$R^{14}$ independently are hydrogen, halogen, hydroxy, oxygen, thiol, amino, alkyl amino, alkoxy, sulfur, imino, iminium, alkyl imino, or alkyl iminium. $R^{15}$ is hydrogen, halogen, hydroxy, oxygen, thiol, amino, alkyl amino, alkoxy, sulfur, imino, iminium, alkyl imino, or alkyl iminium, or a diselenide moiety.

In any of the above embodiments, $X^1$ is O, S, Se, $Si(R^a)(R^b)$, $Ge(R^a)(R^b)$, $Sn(R^a)(R^b)_2$, $C(R^a)(R^b)_2$, or $NR^b$ where $R^a$ is H or $C_1$-$C_{10}$ alkyl and $R^b$ is H, $C_1$-$C_{10}$ alkyl, —COOH, or —$COOR^c$ where $R^c$ is $C_1$-$C_{10}$ alkyl or a conjugatable moiety. In some embodiments, $X^1$ is O, S, Se, $Si(CH_3)_2$, $Ge(CH_3)_2$, $Sn(CH_3)_2$, $CH_2$, $C(CH_3)_2$, or NH. In certain embodiments, $X^1$ is O, Se, $Si(R^a)(R^b)$ or $NR^b$. In some examples, $X^1$ is O.

In any of the above embodiments, $R^1$ is hydrogen, hydroxyl, halogen, thiol, amino, alkyl amino, oxygen, sulfur, imino, iminium, alkyl imino, alkyl iminium, cycloalkyl imino, or a diselenide moiety, and $R^2$ and $R^3$ independently are hydrogen, hydroxy, thiol, $C_1$-$C_{10}$ alkyl, carboxyalkyl, amino, alkoxy, or halogen, or $R^1$-$R^3$ together with Ring A form a tricyclic ring with a nitrogen at $R^1$ and a single bond between $R^1$ and ring A. In some embodiments, $R^1$ is hydrogen, hydroxyl, halogen, thiol, amino, alkyl amino, oxygen, sulfur, imino, iminium, alkyl imino, alkyl iminium, cycloalkyl imino, or a diselenide moiety, and $R^2$ and $R^3$ are hydrogen. In certain embodiments, $R^1$ is a diselenide moiety, hydroxyl, alkyl iminium (e.g., =$N(CH_3)_2^+$), oxygen, or thiol. In such embodiments, $R^2$ and $R^3$ may be hydrogen. In one embodiment, $R^1$-$R^3$ together with Ring A form a tricyclic ring system with a nitrogen at $R^1$ and a single bond between $R^1$ and ring A. The tricyclic ring system may be a 1-azatricyclo[7.3.1.0]trideca-5(13),6,8-triene system.

In any of the above embodiments, $R^4$-$R^6$ independently are hydrogen, hydroxy, thiol, $C_1$-$C_{10}$ alkyl, carboxyalkyl, amino, alkoxy, or halogen. In some embodiments, $R^4$-$R^6$ are hydrogen. In some embodiments, $R^1$ is a diselenide moiety, hydroxyl, alkyl iminium (e.g., $=N(CH_3)_2^+$), or oxygen, and $R^2$-$R^6$ are hydrogen.

In any of the above embodiments, $R^7$, $R^8$, and $R^{10}$ independently are hydrogen, alkyl, acyl, carboxyl, nitro, amino, alkyl amino, —$SO_3H$, —COOH, or —COOR$^d$ where R$^d$ is $C_1$-$C_{10}$ alkyl or a conjugatable moiety. In some embodiments, $R^7$, $R^8$, and $R^{10}$ are hydrogen. In certain embodiments, $R^7$ and $R^{10}$ are hydrogen, and $R^8$ is hydrogen, —COOH, or —COOR$^d$ where R$^d$ is $C_1$-$C_{10}$ alkyl or a conjugatable moiety.

In any of the above embodiments, $R^9$ is hydrogen, alkyl, acyl, carboxyl, nitro, amino, alkyl amino, —$SO_3H$, a diselenide moiety, —COOH, or —COOR$^d$ where R$^d$ is $C_1$-$C_{10}$ alkyl or a conjugatable moiety. In some embodiments, $R^9$ is hydrogen. In certain embodiments, $R^9$ is hydrogen, —COOH, or —COOR$^d$ where R$^d$ is $C_1$-$C_{10}$ alkyl or a conjugatable moiety. In an independent embodiment, $R^9$ is a diselenide moiety.

In any of the above embodiments, $R^{11}$ is one or more atoms forming a ring system with rings C and B and the bond depicted as "-----" in ring C is a single bond, or $R^{11}$ is —COOH, —COO$^-$ or —COOR$^e$ where R$^e$ is $C_1$-$C_{10}$ alkyl or a counter ion with a net single positive charge and the bond depicted as "-----" in ring C is a double bond. Suitable counter ions with a net single positive charge include, but are not limited to, an alkali metal ion, such as K$^+$, Na$^+$, Li$^+$; an ammonium ion, or an alkaline metal earth ion, such as [Ca$^{2+}$]$_{0.5}$, [Mg$^{2+}$]$_{0.5}$, or [Ba$^{2+}$]$_{0.5}$ (a subscript "0.5" means, for example, that one of the counter ions for such divalent alkali earth ions can be an ionized form of a compound as disclosed herein and the other a typical counter ion such as chloride, or two ionized compounds can serve as counter ions for such divalent alkali earth ions). In some embodiments, $R^{11}$ is —COOH, —COO$^-$ or —COOR$^e$ where R$^e$ is $C_1$-$C_{10}$ alkyl or a counter ion with a net single positive charge and the bond depicted as "-----" in ring A is a double bond. In some embodiments, $R^{11}$ is —COOH, —COO$^-$ or —COOR$^e$ where R$^e$ is a counter ion with a net single positive charge. In certain embodiments, when the compound is in an aqueous solution, $R^{11}$ is —COO$^-$. In some embodiments, $R^{11}$ is one or more atoms forming a ring system with rings C and B and the bond depicted as "-----" in ring C is a single bond. $R^{11}$ may be, for example, —C(O)—O—, thereby forming a lactone ring.

In any of the above embodiments, when the compound has a structure according to Formula II, $R^{12}$-$R^{14}$ independently are hydrogen, halogen, hydroxy, oxygen, thiol, amino, alkyl amino, alkoxy, sulfur, imino, iminium, alkyl imino, or alkyl iminium. In some embodiments, $R^{12}$ and $R^{14}$ are hydrogen, and $R^{13}$ is hydrogen, hydroxyl or thiol. In certain embodiments, $R^{12}$-$R^{14}$ are hydrogen.

In any of the above embodiments, when the compound has a structure according to Formula II, $R^{15}$ is hydrogen, halogen, hydroxy, oxygen, thiol, amino, alkyl amino, alkoxy, sulfur, imino, iminium, alkyl imino, or alkyl iminium, or a diselenide moiety. In some embodiments, $R^{15}$ is alkoxy or a diselenide moiety. The alkoxy may be a $C_1$-$C_{10}$ alkoxy, such as a $C_1$-$C_5$ alkoxy or a $C_1$-$C_3$ alkoxy, e.g., methoxy or ethoxy. In some examples, $R^{15}$ is methoxy or a diselenide moiety, and $R^{12}$-$R^{14}$ are hydrogen.

The compound includes at least one diselenide moiety. In some embodiments, the compound includes a diselenide moiety at $R^1$, $R^9$, or $R^{15}$. In certain embodiments, the compound includes two diselenide moieties, e.g., at $R^1$ and $R^{15}$, $R^1$ and $R^9$, or $R^9$ and $R^{15}$. The compound may include three diselenide moieties. Each diselenide moiety independently has a formula —Y—C(Q)O—(CH$_2$)$_m$—Se—Se—(CH$_2$)$_n$—OR$^f$, where R$^f$ is hydrogen or $C_1$-$C_3$ alkyl, Q is O or S, Y is O or N(R$^g$) where R$^g$ is H or alkyl, and m and n independently are integers from 1-5, i.e., 1, 2, 3, 4, or 5. In some embodiments, Y is O or N(H). In any of the foregoing embodiments, R$^f$ may be H. In any of the foregoing embodiments, m may be 2, n may be 2, or m and n may both be 2. Exemplary diselenide moieties include, but are not limited to, —N(H)C(O)O(CH$_2$)$_2$Se—Se(CH$_2$)$_2$OH, —OC(O)O(CH$_2$)$_2$Se—Se(CH$_2$)$_2$OH, —N(H)C(S)O(CH$_2$)$_2$Se—Se(CH$_2$)$_2$OH, and —OC(S)O(CH$_2$)$_2$Se—Se(CH$_2$)$_2$OH.

In any of the above embodiments, the compound may include a conjugatable moiety, e.g., at $X^1$ or one of $R^7$-$R^{10}$. In some embodiments, the compound includes a conjugatable moiety at $R^8$ or $R^9$. Suitable conjugatable moieties include, but are not limited to, —$SO_2Cl$, N-hydroxysuccinimidyl groups, maleimidyl groups, —NCO, —NCS, alkenyl groups, alkynyl groups, azides, tetrazines, phosphoramidites, and combinations thereof. In some embodiments, the conjugatable moiety is —$SO_2Cl$, a N-hydroxysuccinimidyl group, or —NCO. The conjugatable group may be used to conjugate the seminaphthofluorophore to a targeting agent. Exemplary targeting agents include, but are not limited to, antibodies, antibody fragments, ligands, peptides, nucleic acid strands, polysaccharides, and the like.

In some embodiments, the compound is:

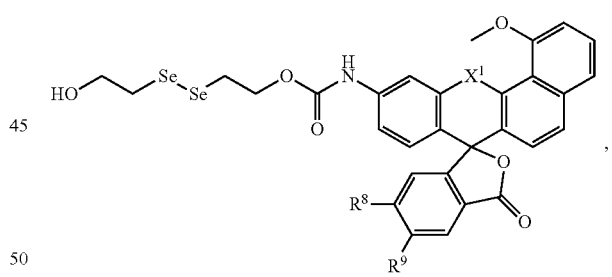

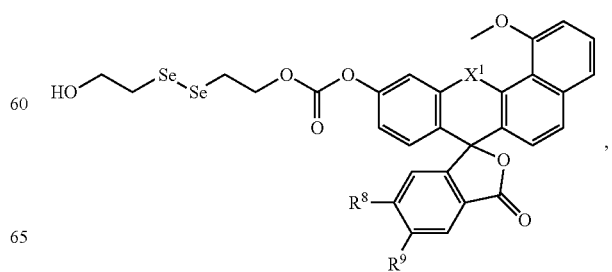

11
-continued
12
-continued
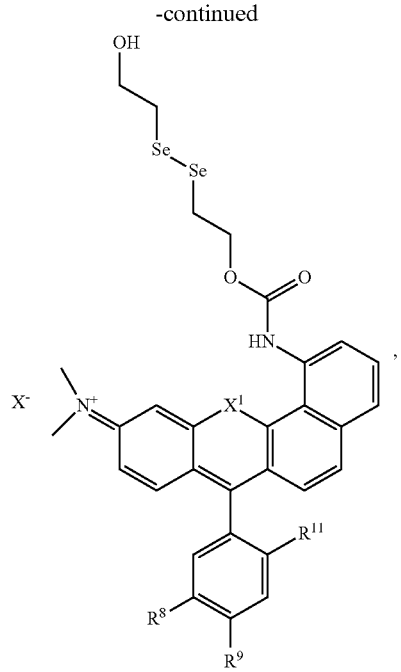
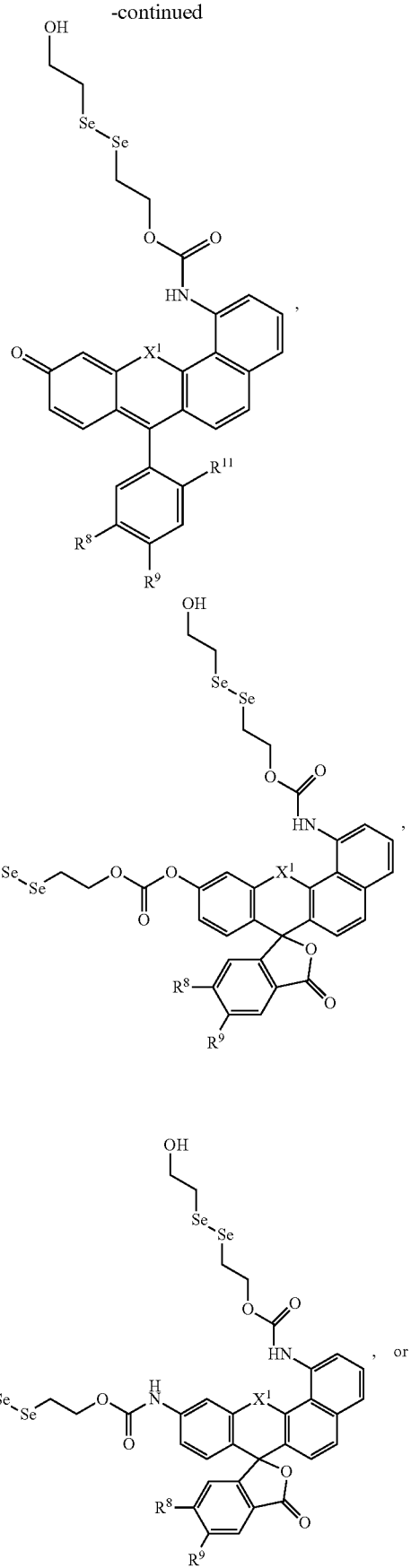

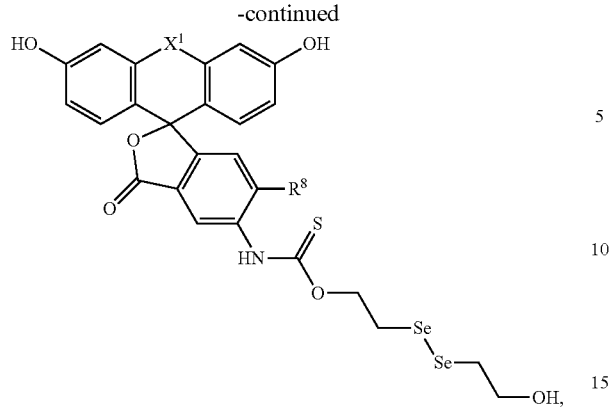

where $X^1$ is O, Se, or $Si(R^a)(R^b)$; $X^-$ is absent or a counter ion with a net single negative charge; $R^8$ and $R^9$ independently are hydrogen, alkyl, acyl, carboxyl, nitro, amino, alkyl amino, —$SO_3H$, —COOH, or —$COOR^d$ where $R^d$ is $C_1$-$C_{10}$ alkyl or a conjugatable moiety; and $R^{11}$ is —COOH, —COO⁻, or —$COOR^e$ where $R^e$ is a counter ion with a net single positive charge. In some embodiments, $X^1$ is O. In any of the foregoing embodiments, $R^8$ and $R^9$ independently may be H, —COOH, or —$COOR^d$ where $R^d$ is $C_1$-$C_{10}$ alkyl or a conjugatable moiety.

Exemplary compounds include, but are not limited to:

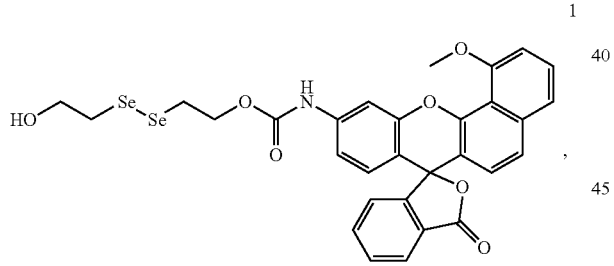

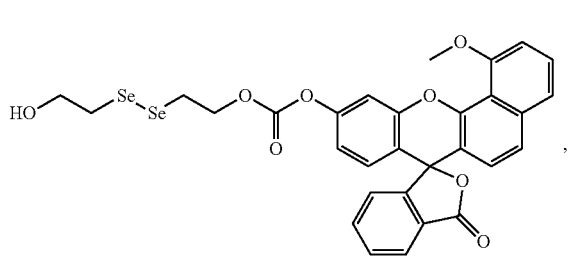

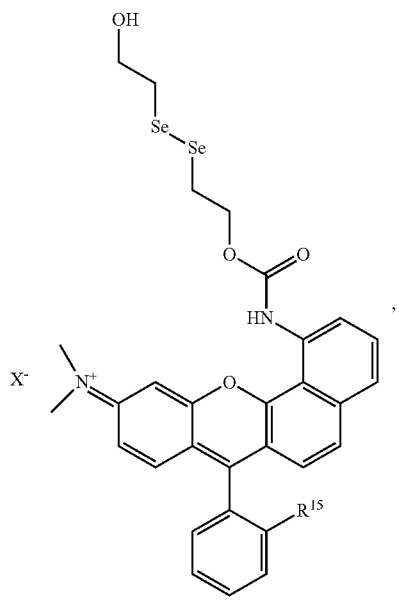

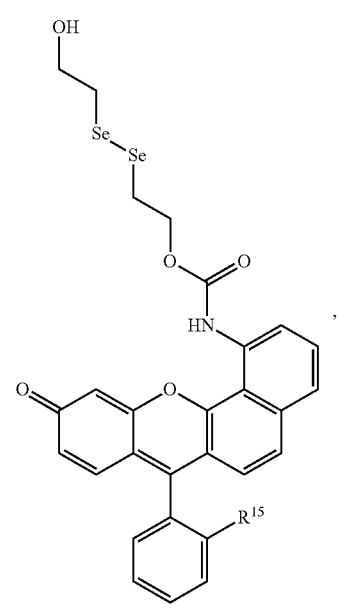

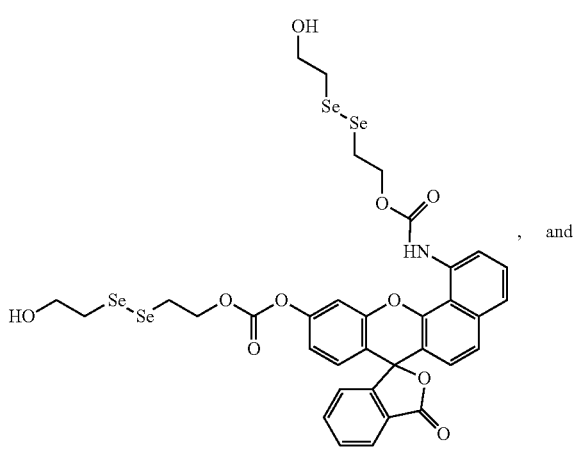

, and

-continued

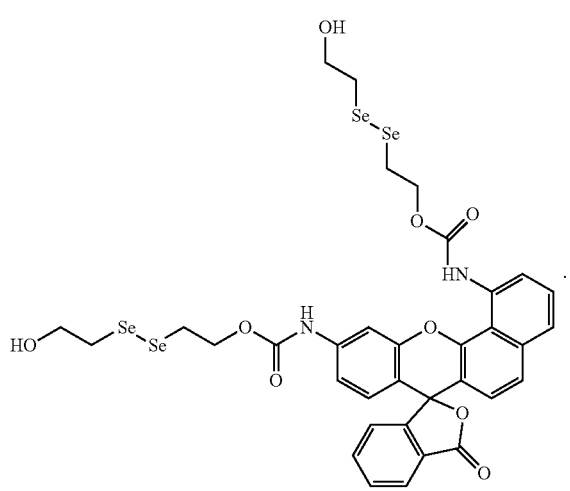

6

Table 1 shows the maximum absorbance and emission wavelengths for the seminaphthofluorophore scaffold (without the diselenide moiety/moieties) of each of compounds 1-6 in 10% DMSO, 100 mM phosphate buffer, pH 7.4.

TABLE 1

| Compound | $\lambda_{max, abs}$ (nm) | $\lambda_{max, em}$ (nm) |
|---|---|---|
| 1 | 531 | 580 |
| 2 | 531 | 580 |
| 3 | 598 | 770 |
| 4 | 549 | 750 |
| 5 | 549 | 750 |
| 6 | 576 | 760 |

III. METHODS OF USE

Embodiments of the disclosed seminaphthofluorophore-selenium probes may be used to detect presence of a thioredoxin reductase. In the presence of a thioredoxin reductase and NADPH, a nucleophilic attack of the diselenide bond occurs through a selenocystine residue on the enzyme. The selenolate formed attacks the carbamate carbonyl, and an oxaselenolanone heterocycle and the seminaphthofluorophore scaffold are released. The proposed mechanism is shown below with compound 1 and TrxR1 as an example. Release of the seminaphthofluorophore scaffold results in a color change and/or change in the fluorescence emission spectrum (e.g., a shift in the emission maximum, a fluorescence increase) of the compound.

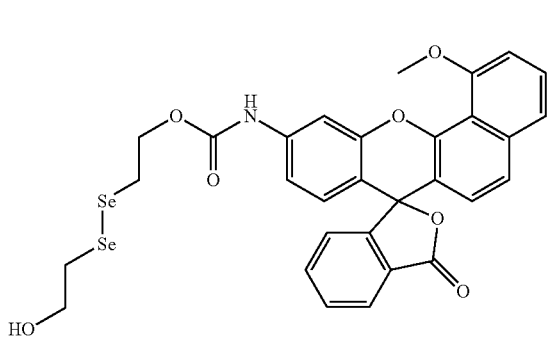

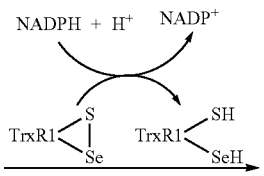

1

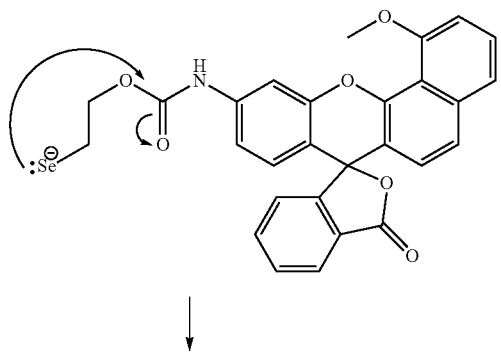

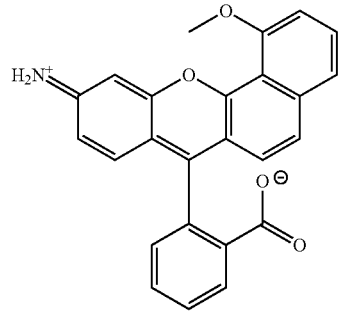

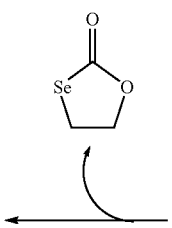

Oxaseleonolanone

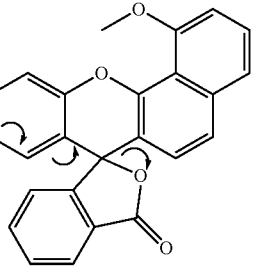

2

Advantageously, some embodiments of the disclosed compounds do not fluoresce when the diselenide moiety is present. Upon cleavage of the diselenide moiety, the released seminaphthofluorophore scaffold fluoresces when excited by light having a suitable wavelength, e.g., 500-600 nm. In some embodiments, the fluorescence emission maximum is at a wavelength>550 nm, such as a wavelength within a range of 575-800 nm. In certain embodiments, the disclosed compounds are selective to thioredoxin reductases and do not react with other biological thiols (e.g., cysteine, homocysteine, glutathione) or sulfur-containing ions (e.g., sulfide, sulfite, sulfate, thiosulfate).

Although thioredoxin reductases may react with disulfide-containing probes, the diselenide bond has a lower pKa than a disulfide bond, making seleboates better leaving groups at physiological pH. The diselenide bond is also more susceptible to nucleophilic attack by the TrxR1 selenocysteine residue, partly due to selenium's larger atomic radius with less steric crowding. Overall, presence of the diselenide bond in the probe is superior to a disulfide bond. Indeed, a selenocysteamine/selenocystamine exchange has been shown to be $2.4 \times 10^5$ times faster than a cysteamine/cystamine exchange (Pleasants et al., *JACS* 1989, 111:6553-6558). The selenolate formed is also ten times more nucleophilic than thiolate (Cowgill, *Biochim Biophys Acta, Protein Struct Mol Enzymol* 1967, 140:37-44). The cyclization process to uncage the seminaphthofluorophore scaffold is therefore faster when the probe includes a diselenide moiety as disclosed herein.

In some embodiments, a compound as disclosed herein is combined with a biological sample comprising, or suspected of comprising, a thioredoxin reductase. A reaction between the biological sample and the compound is allowed to proceed for an effective period of time to produce a detectable change in the compound's color or emission spectrum, and the change is detected. Combining the compound with the biological sample may be performed ex vivo, e.g., by combining a tissue sample biopsy with the compound. In certain embodiments, combining may be performed in vivo, e.g., by applying a pharmaceutical composition, such as a topical composition (e.g., a lotion, cream, or ointment), comprising the compound to an area of skin on a subject. The detectable change indicates that the thioredoxin reductase is present in the biological sample. In some embodiments, the thioredoxin reductase is TrxR1. In any of the foregoing embodiments, detecting the change may be performed by visual inspection, spectrophotometry, or emission spectroscopy.

In any of the above embodiments, the effective time may be 1-60 minutes. The effective time is sufficient for the thioredoxin reductase, if present, to cleave the diselenide moiety or diselenide moieties from at least some molecules of the compound, thereby producing a seminaphthofluorophore.

In any of the above embodiments, the seminaphthofluorophore may have a fluorescence emission maximum at a wavelength within a range of 550-800 nm. In some embodiments, detecting the change in the compound's emission spectrum comprises detecting an increase in fluorescence intensity at a wavelength within a range of 550-800 nm, such as within a range of 570-590 nm. In certain embodiments, detecting the changes comprises detecting a visible change in the compound's color, e.g., the color of the compound in a solution comprising the compound. In some embodiments, the sample includes an increased amount of thioredoxin reductase relative to a control sample from a subject without a condition characterized at least in part by altered thioredoxin reductase levels, and the fluorescence intensity will be greater in the sample compared to fluorescence in the control sample. In other embodiments, the sample may include a reduced amount of thioredoxin reductase relative to a control sample from a subject without a condition characterized at least in part by altered thioredoxin reductase levels, and the fluorescence intensity will be lower in the sample compared to fluorescence in the control sample. For example, subjects with Parkinson's Disease may have reduced thioredoxin reductase levels in neurological tissue compared to healthy subjects.

In any of the above embodiments, the biological sample may comprise a tissue sample. In some embodiments, the tissue sample includes cancer cells or neurological tissue. The cancer cells may comprise melanoma cells, lung carcinoma cells, or prostate cancer cells, among others. In some embodiments, combining the compound with the biological sample comprises combining the tissue sample and a solution comprising the compound, phosphate-buffered saline pH 7.0-7.5, and DMSO. In some embodiments, the tissue sample may be a tissue biopsy and combining is performed in vitro or ex vivo.

In some embodiments, a method for determining presence of a thioredoxin reductase comprises providing a compound selected from

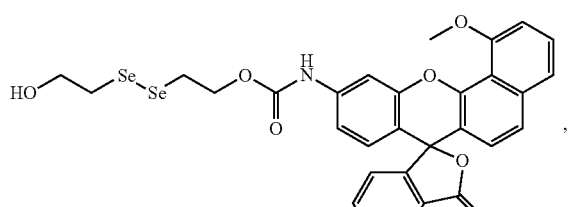
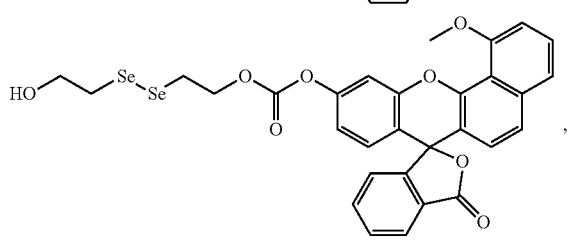
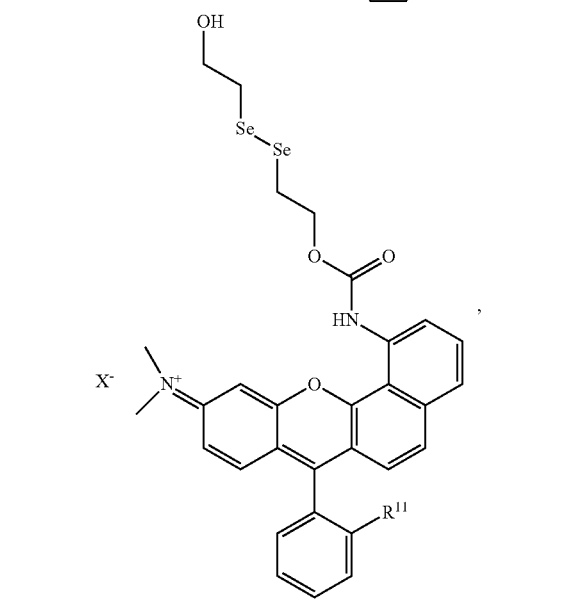
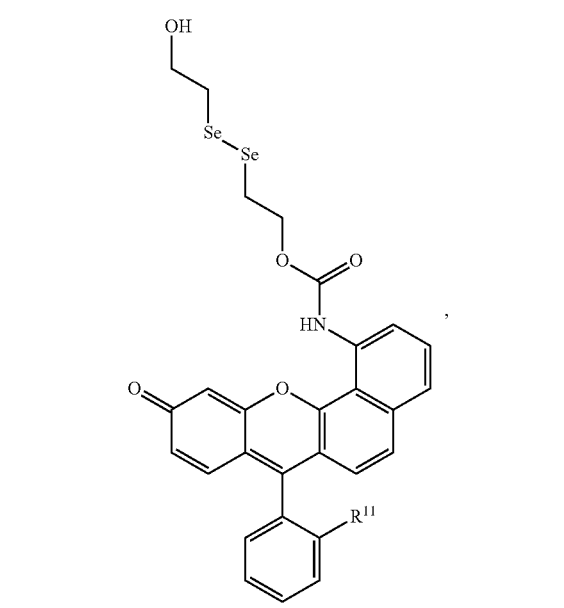

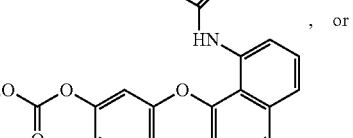
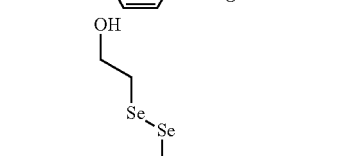
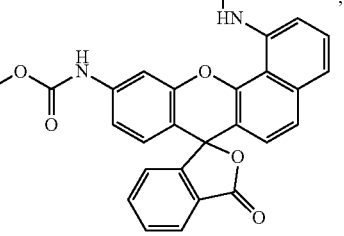

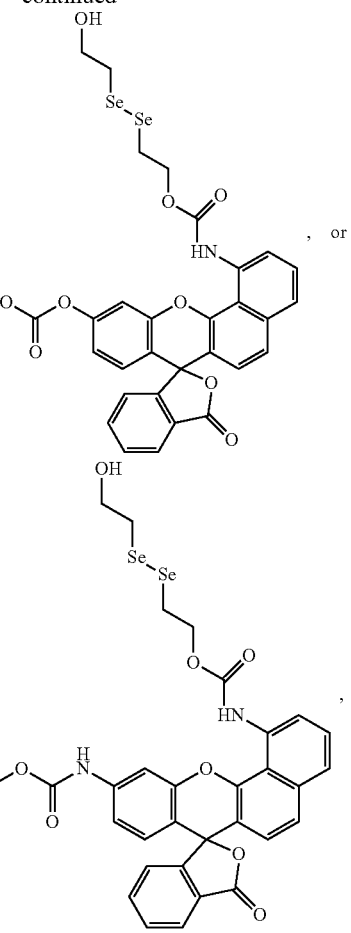

where X⁻ is absent or a counter ion with a net single negative charge, and $R^{11}$ is —COOH, —COO⁻, or —COOR$^e$ where $R^e$ is a counter ion with a net single positive charge; combining the compound with a biological sample; allowing a reaction between the biological sample and the compound to proceed for an effective period of time of from 1 to 60 minutes to produce a seminaphthofluorophore having a fluorescence emission maximum at a wavelength within a range of 550-800 nm if thioredoxin reductase is present in the biological sample; and analyzing the solution by visual inspection, spectrophotometry, or emission spectroscopy to detect a color change or an increase in fluorescence intensity at a wavelength within a range of 570-590 nm after the effective period of time if thioredoxin reductase is present in the biological sample.

In any of the above embodiments, the compound may be

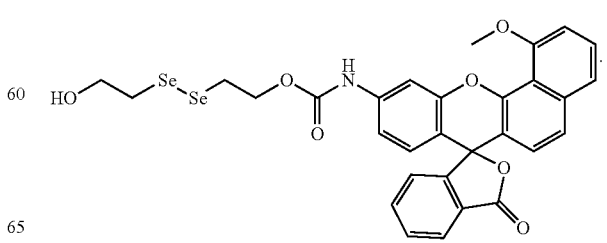

III. REPRESENTATIVE EMBODIMENTS

Certain representative embodiments are exemplified in the following paragraphs.

A compound according to Formula I, or an ionized form or salt thereof:

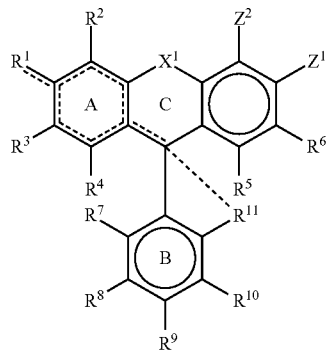

(I)

where each bond depicted as "-----" is a single or double bond as needed to satisfy valence requirements; $Z^1$ and $Z^2$ independently are hydrogen, hydroxyl, or thiol, or $Z^1$ and $Z^2$ together with the atoms to which they are attached form a substituted or unsubstituted 6-membered ring; $X^1$ is O, S, Se, $Si(R^a)(R^b)$, $Ge(R^a)(R^b)$, $Sn(R^a)(R^b)_2$, $C(R^a)(R^b)_2$, or $NR^b$ where $R^a$ is H or $C_1$-$C_{10}$ alkyl and $R^b$ is H, $C_1$-$C_{10}$ alkyl, —COOH, or —COOR$^c$ where $R^c$ is $C_1$-$C_{10}$ alkyl or a conjugatable moiety; $R^1$ is hydrogen, hydroxyl, halogen, thiol, amino, alkyl amino, oxygen, sulfur, imino, iminium, alkyl imino, alkyl iminium, cycloalkyl imino, or a diselenide moiety, and $R^2$ and $R^3$ independently are hydrogen, hydroxy, thiol, $C_1$-$C_{10}$ alkyl, carboxyalkyl, amino, alkoxy, or halogen, or $R^1$-$R^3$ together with Ring A form a tricyclic ring system with a nitrogen at $R^1$ and a single bond between $R^1$ and ring A; $R^4$-$R^6$ independently are hydrogen, hydroxy, thiol, $C_1$-$C_{10}$ alkyl, carboxyalkyl, amino, alkoxy, or halogen; $R^7$, $R^8$, and $R^{10}$ independently are hydrogen, alkyl, acyl, carboxyl, nitro, amino, alkyl amino, —SO$_3$H, —COOH, or —COOR$^d$ where $R^d$ is $C_1$-$C_{10}$ alkyl or a conjugatable moiety; $R^9$ is hydrogen, alkyl, acyl, carboxyl, nitro, amino, alkyl amino, —SO$_3$H, a diselenide moiety, —COOH, or —COOR$^d$ where $R^d$ is $C_1$-$C_{10}$ alkyl or a conjugatable moiety; and $R^{11}$ is one or more atoms forming a ring system with rings C and B and the bond depicted as "-----" in ring C is a single bond, or $R^{11}$ is —COOH, —COO$^-$ or —COOR$^e$ where $R^e$ is $C_1$-$C_{10}$ alkyl or a counter ion with a net single positive charge and the bond depicted as "-----" in ring C is a double bond, wherein the compound comprises at least one diselenide moiety, and each diselenide moiety independently has a formula —Y—C(Q)O—(CH$_2$)$_m$—Se—Se—(CH$_2$)$_n$—OR$^f$, where R$^f$ is hydrogen or $C_1$-$C_8$alkyl, Q is O or S, Y is O or N(R$^g$) where R$^g$ is H or alkyl, and m and n independently are integers from 1-5.

The compound of the foregoing paragraph where $Z^1$ and $Z^2$ together with the atoms to which they are attached form a substituted or unsubstituted 6-membered ring and the compound has a structure according to Formula II, or an ionized form or salt thereof:

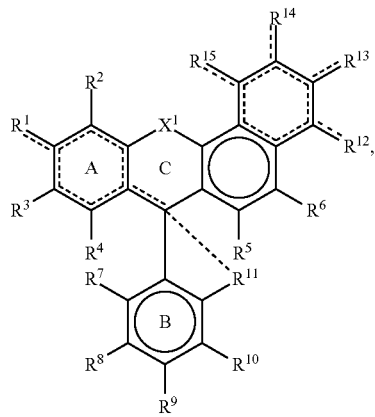

(II)

wherein $R^{12}$-$R^{14}$ independently are hydrogen, halogen, hydroxy, oxygen, thiol, amino, alkyl amino, alkoxy, sulfur, imino, iminium, alkyl imino, or alkyl iminium; and $R^{15}$ is hydrogen, halogen, hydroxy, oxygen, thiol, amino, alkyl amino, alkoxy, sulfur, imino, iminium, alkyl imino, or alkyl iminium, or a diselenide moiety.

The compound of any of the foregoing paragraphs where $X^1$ is O, Se, Si(R$^a$)(R$^b$), or NR$^b$.

The compound of any of the foregoing paragraphs where: $R^{11}$ is —COO— and forms a lactone ring; or $R^{11}$ is —COOH, —COO$^-$ or —COOR$^e$ where R$^e$ is a counter ion with a net single positive charge.

The compound of any of the foregoing paragraphs where: (i) $R^2$-$R^4$ are hydrogen; or (ii) $R^5$ and $R^6$ are hydrogen; or (iii) $R^7$ and $R^{10}$ are hydrogen; or (iv) $R^8$ and $R^9$ independently are hydrogen or —COOR$^d$, or (v) $R^{12}$-$R^{14}$ are hydrogen; or (vi) any combination of (i), (ii), (iii), (iv) and (v).

The compound according to Formula II of any of the foregoing paragraphs where: $R^1$ is —Y—C(Q)O—(CH$_2$)$_m$—Se—Se—(CH$_2$)$_n$—OR$^f$; and $R^{15}$ is $C_1$-$C_3$ alkoxy or hydroxy. The compound according to Formula II of any of the foregoing paragraphs where: $R^1$ is O or alkyl iminium; and $R^{15}$ is —Y—C(Q)O—(CH$_2$)$_m$—Se—Se—(CH$_2$)$_n$—OR$^f$. The compound according to Formula II of any of the foregoing paragraphs where both $R^1$ and $R^{15}$ independently are —Y—C(Q)O—(CH$_2$)$_m$—Se—Se—(CH$_2$)$_n$—OR$^f$.

The compound according to Formula I of any of the foregoing paragraphs where: $Z^1$ is hydroxyl or thiol; $Z^2$ is hydrogen; $R^1$ is hydroxyl or thiol; and $R^9$ is —Y—C(Q)O—(CH$_2$)$_m$—Se—Se—(CH$_2$)$_n$—OR$^f$.

The compound of any of the foregoing paragraphs where: (i) m is 2; or (ii) n is 2; or (iii) R$^f$ is H; or (iv) Y is O or N(H); or (v) any combination of (i), (ii), (iii), and (iv).

The compound as disclosed herein where the compound is

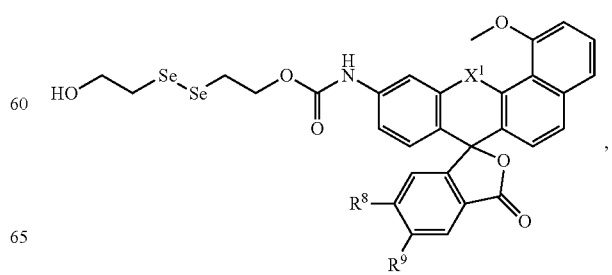

,

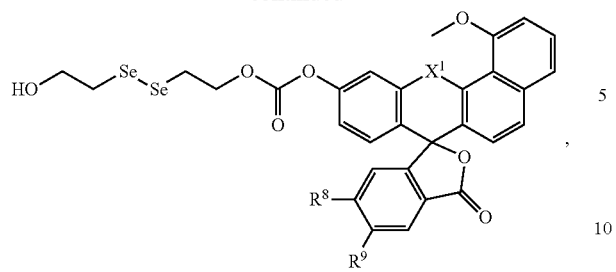
,
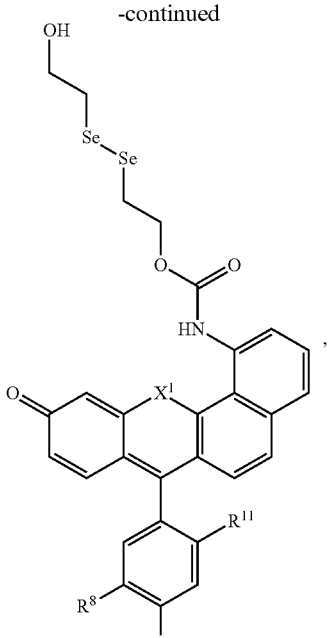
,
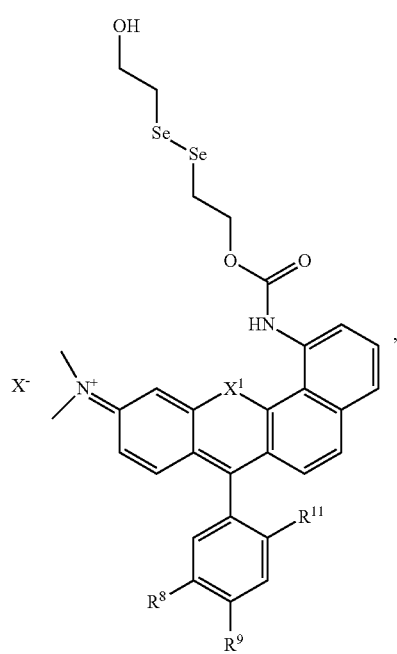
,
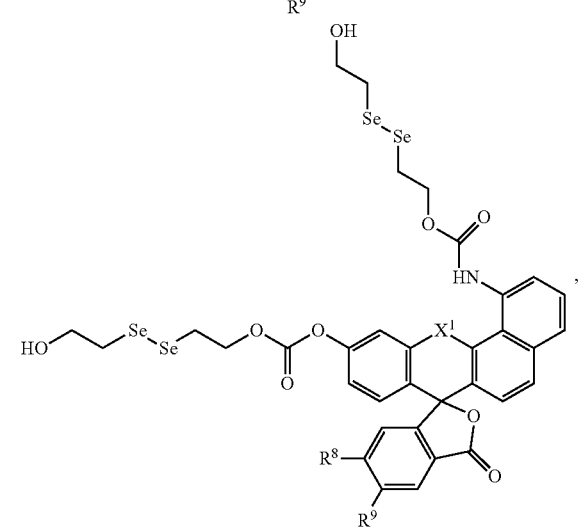
,
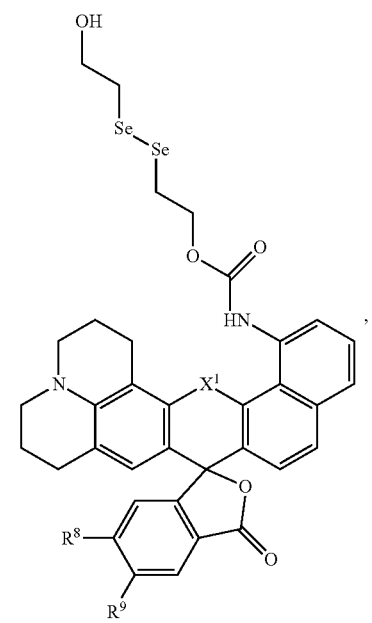
,
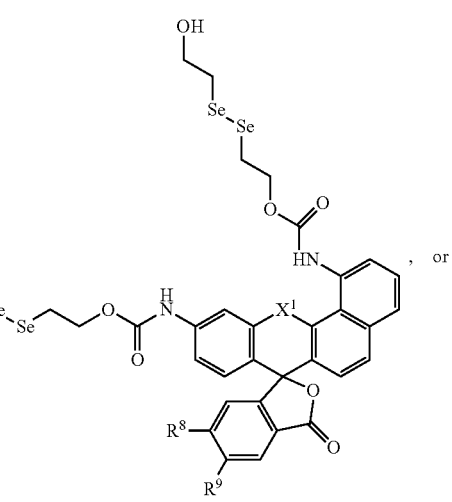
, or
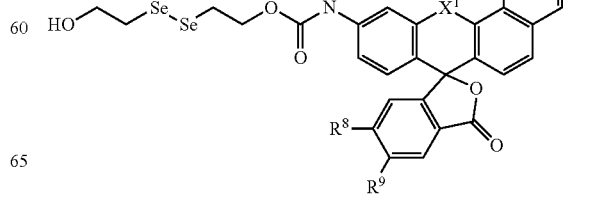

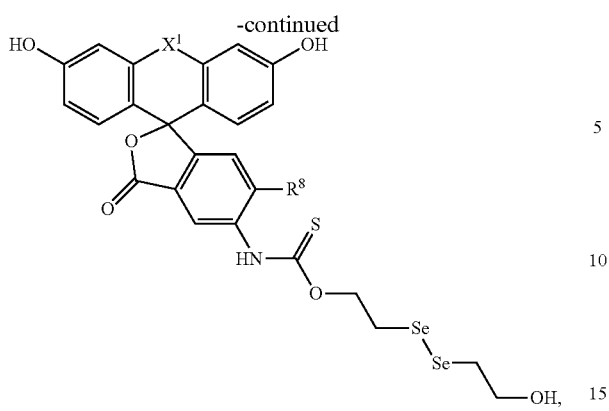

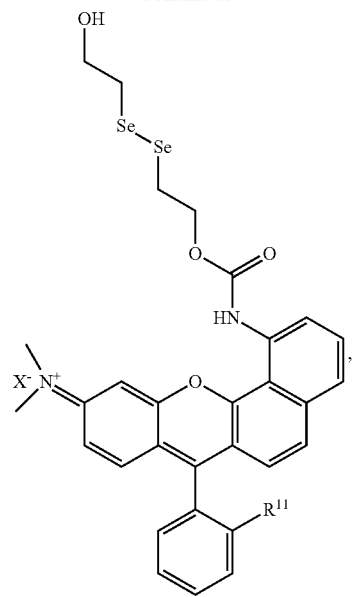

where $X^1$ is O, Se, or $Si(R^a)(R^b)$; $X^-$ is absent or a counter ion with a net single negative charge; $R^8$ and $R^9$ independently are hydrogen, alkyl, acyl, carboxyl, nitro, amino, alkyl amino, —$SO_3H$, —COOH, or —$COOR^d$ where $R^d$ is $C_1$-$C_{10}$ alkyl or a conjugatable moiety; and $R^{11}$ is —COOH, —COO$^-$, or —$COOR^e$ where $R^e$ is a counter ion with a net single positive charge.

The compound as disclosed herein where the compound is

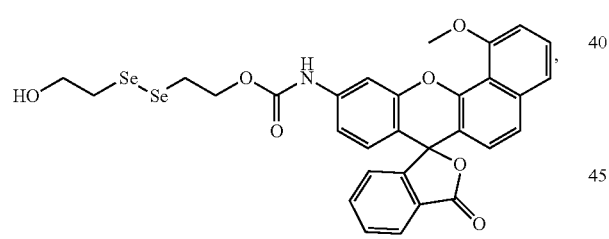

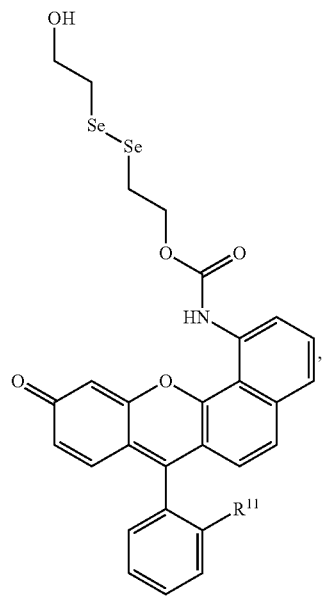

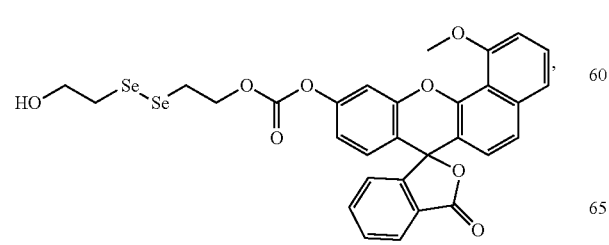

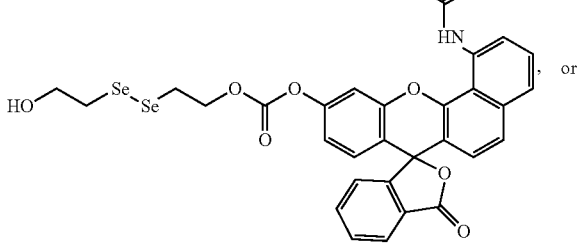

-continued

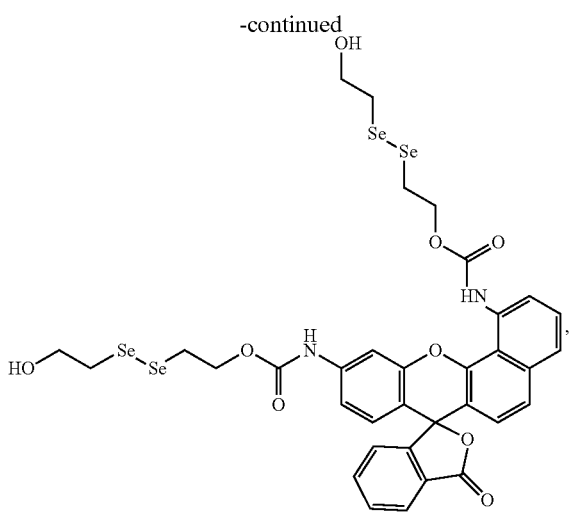

where X⁻ is absent or a counter ion with a net single negative charge, and $R^{11}$ is —COOH, —COO⁻, or —COOR$^e$ where $R^e$ is a counter ion with a net single positive charge.

A method for determining presence of a thioredoxin reductase, comprising: combining a compound according to any of the foregoing paragraphs with a biological sample comprising, or suspected of comprising, a thioredoxin reductase; allowing a reaction between the biological sample and the compound to proceed for an effective period of time to produce a detectable change in the compound's color or emission spectrum, where the detectable change indicates that the thioredoxin reductase is present in the biological sample; and detecting the change.

The method of the foregoing paragraph where the thioredoxin reductase comprises TrxR1.

The method of any of the foregoing paragraphs where the effective time is 1-60 minutes.

The method of any of the foregoing paragraphs where the effective time is sufficient for the thioredoxin reductase to cleave the diselenide moiety or diselenide moieties from at least some molecules of the compound, thereby producing a seminaphthofluorophore.

The method of the foregoing paragraph where the seminaphthofluorophore has a fluorescence emission maximum at a wavelength within a range of 550-800 nm.

The method of any of the foregoing paragraphs where detecting the change comprises detecting an increase in fluorescence intensity at a wavelength within a range of 570-590 nm after the effective period of time.

The method of any of the foregoing paragraphs where the biological sample comprises a tissue sample.

The method of the foregoing paragraph where the biological sample includes cancer cells or neurological tissue.

The method of the foregoing paragraph where the cancer cells comprise melanoma cells, lung carcinoma cells, or prostate cancer cells.

The method of any of the foregoing paragraphs where combining the compound with the biological sample comprises combining the tissue sample and a solution comprising the compound, phosphate-buffered saline pH 7.0-7.5, and DMSO.

A method for determining presence of a thioredoxin reductase, comprising:
providing a compound selected from

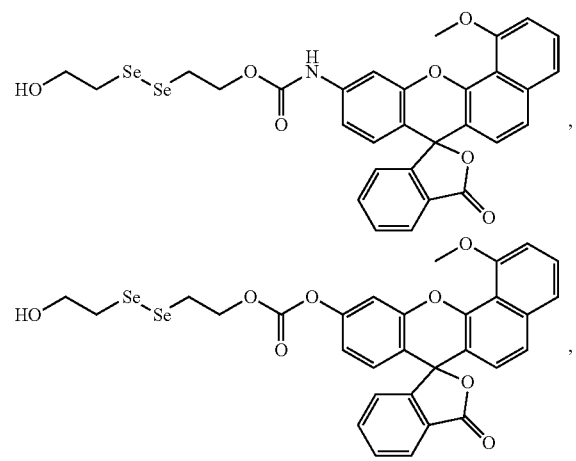

-continued

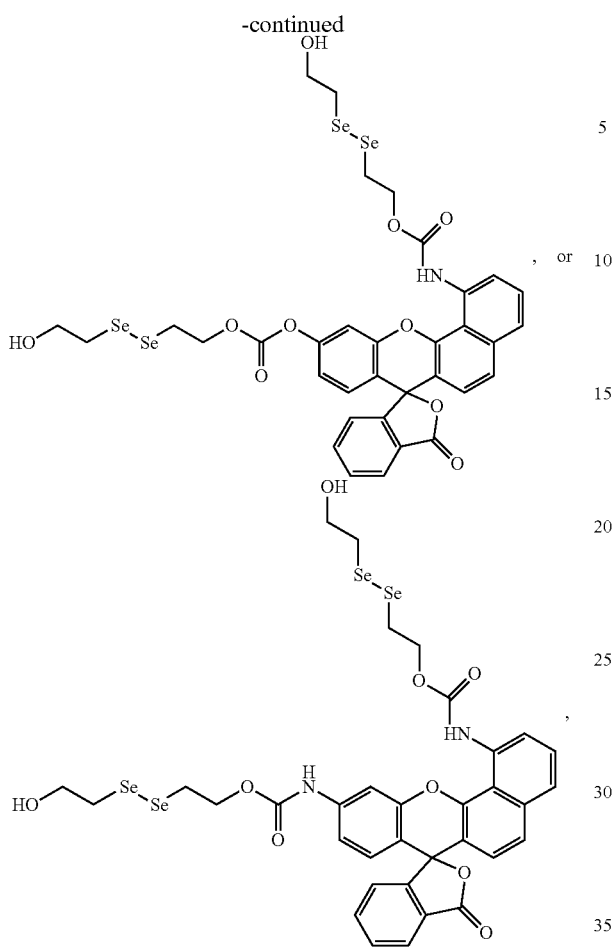

, or where $X^-$ is absent or a counter ion with a net single negative charge, and $R^{11}$ is —COOH, —COO$^-$, or —COOR$^e$ where $R^e$ is a counter ion with a net single positive charge; combining the compound with a biological sample; allowing a reaction between the biological sample and the compound to proceed for an effective period of time of from 1 to 60 minutes to produce a seminaphthofluorophore having a fluorescence emission maximum at a wavelength within a range of 550-800 nm if thioredoxin reductase is present in the biological sample; and analyzing the solution by visual inspection, spectrophotometry, or emission spectroscopy after the effective period of time to detect a color change or an increase in fluorescence intensity at a wavelength within a range of 570-590 nm if thioredoxin reductase is present in the biological sample.

The method of the foregoing paragraph where the compound is

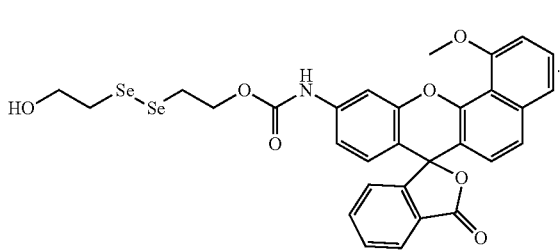 [SMILES: COc1cccc2ccc3c(c12)Oc1cc(NC(=O)OCC[Se][Se]CCO)ccc1C31OC(=O)c2ccccc21]

A method, comprising combining a compound as recited any of in the foregoing paragraphs with a biological sample comprising, or suspected of comprising, a thioredoxin reductase, wherein combining the compound with the biological sample is performed in vivo.

IV. EXAMPLES

Example 1

Probe Synthesis

Probe 1 was synthesized as shown in Scheme 1:

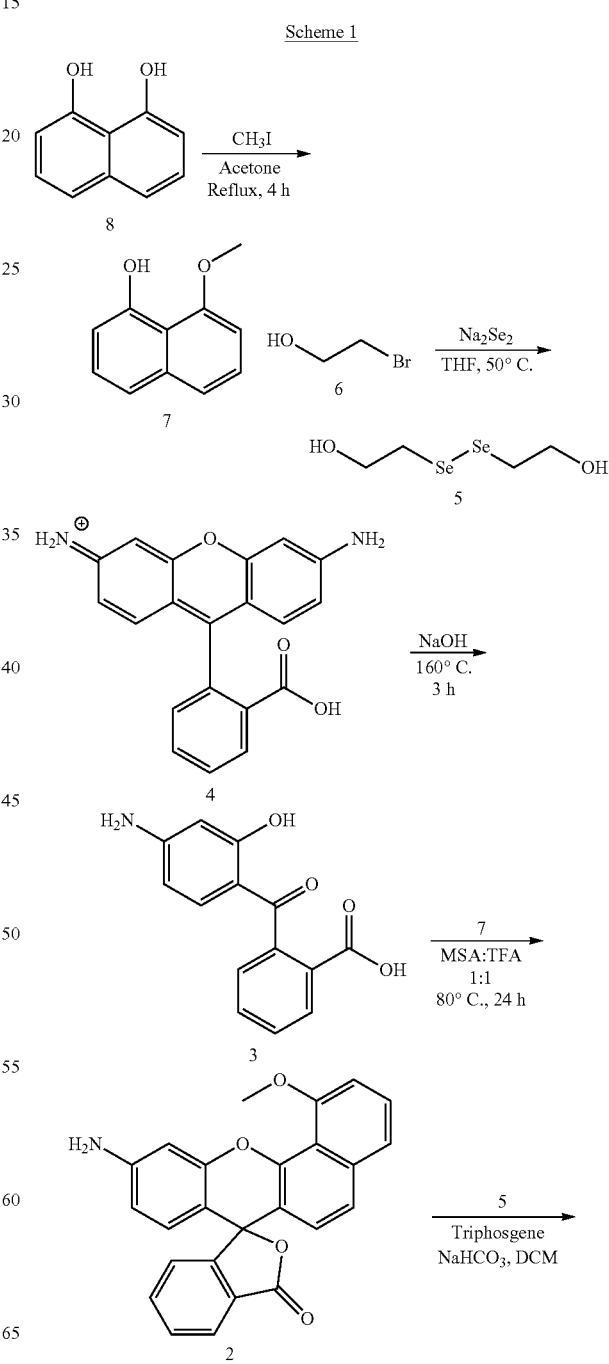

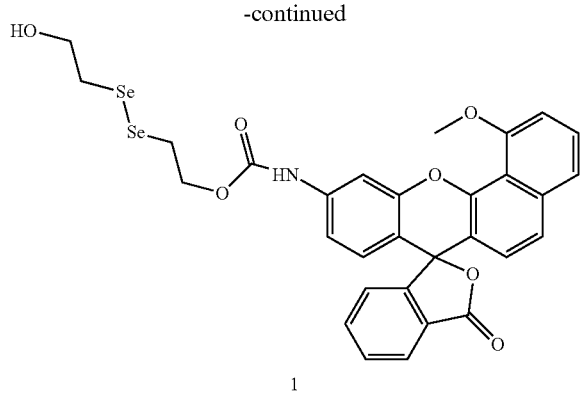

1

Selenium and 2-bromoethanol were purchased from Fischer Scientific (Waltham, MA). All other chemicals, along with Thioredoxin reductase from rat liver were obtained from Sigma-Aldrich (St. Louis, MO) and used without further purification.

Initial absorbance measurements were performed on a Cary Eclipse™ 50 Bio UV-Vis spectrophotometer. Fluorescence measurements were performed on a Cary Eclipse™ fluorescence spectrophotometer (Agilent Technologies, Santa Clara, CA). Absorption and emission measurements for enzymatic assays were carried out on a Synergy H1 microplate reader (BioTek, Winooski, VT) using accompanying Gen5 software version 2.05. LC/MS analysis of the compounds was carried out on an Agilent Technologies 6224 TOF LC/MS. All NMR data was collected on a Bruker 400 MHz Avance™ II+ spectrometer.

Synthesis of 7.

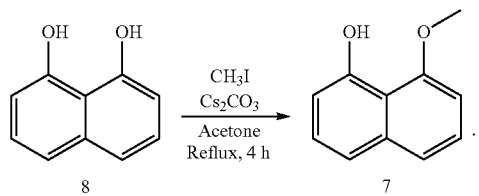

Scheme 2: Synthesis of 8-methoxynaphthalen-1-ol, 7

Under $N_2$, 1,8-dihydroxynaphthalene (8) (1.00 g, 6.24 mmol) and $Cs_2CO_3$ (3.05 g, 9.36 mmol) were suspended in 10 mL of acetone. $CH_3I$ (390 μL, 0.89 g, 6.24 mmol) was added in one portion and the mixture refluxed for 4 h. The mixture was cooled to rt, diluted with 20 mL of $H_2O$ and the pH adjusted to 1 by adding HCl. Liquid-liquid extraction was then done with EtOAc (2×50 mL) and the organic fractions combined and dried over anhydrous $Na_2SO_4$. The $Na_2SO_4$ was filtered off and the solvent removed under vacuum. The crude solid was purified by flash chromatography (silica, EtOAc:Hexanes 1:3). Compound 7 was obtained as a white solid (0.92 g, 84.4%). Low-res ESI-MS (m/z) calc for $C_{11}H_{11}O_2$ [M+H]$^+$: 175.0736, found: 175.0674. $^1$H NMR (400 MHz, DMSO-$d_6$) δ 9.39 (s, 1H), 7.45-7.30 (m, 4H), 6.94 (dd, J=7.6, 1.2 Hz, 1H), 6.79 (dd, J=6.6, 2.1 Hz, 1H), 4.03 (s, 3H). $^{13}$C NMR (101 MHz, DMSO-$d_6$) δ 156.34, 154.33, 136.73, 127.77, 126.64, 121.42, 118.87, 114.56, 110.62, 104.95, 56.01, 40.05.

Synthesis of 3.

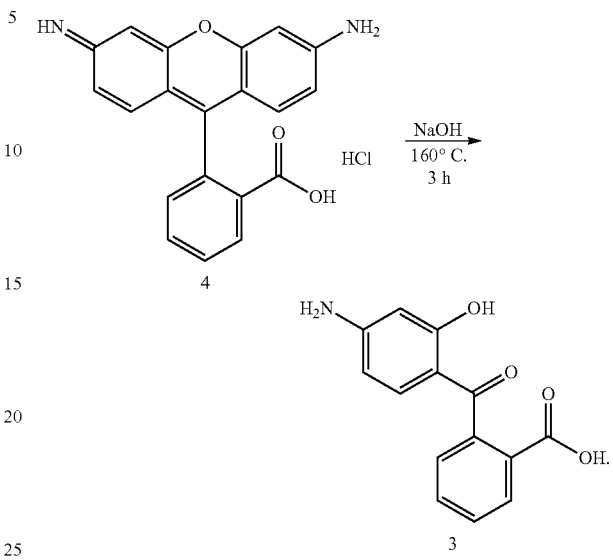

Scheme 3: Synthesis of 2-(4-amino-2-hydroxybenzoyl)benzoic acid, 3

Rhodamine 110 hydrochloride (4) (0.20 g, 0.55 mmol) and NaOH (0.38 g, 9.27 mmol) were dissolved in 180 μL of $H_2O$. The mixture was heated at 160° C. for 2 h, followed by the addition of 0.5 mL of 50% NaOH. After heating at 160° C. for another hour, 10 mL of $H_2O$ was added to the reaction and the pH was adjusted to 1 with HCl. The solution was extracted with EtOAc (2×50 mL) after which the solvent was removed under vacuum to obtain a yellow solid which required no further purification (0.13 g, 94% yield). Low-res ESI-MS (m/z) calc for $C_{14}H_{12}NO_4$ [M+H]$^+$: 258.0761, found: 258.0721. $^1$H NMR (400 MHz, DMSO) δ 13.05 (s, 1H), 12.61 (s, 1H), 7.95 (d, J=7.7 Hz, 1H), 7.68 (t, J=7.5 Hz, 1H), 7.60 (t, J=7.6 Hz, 1H), 7.37 (d, J=7.47 Hz, 1H), 6.72 (d, J=8.5 Hz, 1H), 6.45 (s, 2H), 6.02 (d, J=10.1 Hz 2H). $^{13}$C NMR (101 MHz, DMSO) δ 198.31, 166.92, 164.98, 156.82, 140.07, 134.48, 131.95, 129.84, 129.69, 129.31, 127.68, 109.79, 106.48, 98.16.

Synthesis of 5.

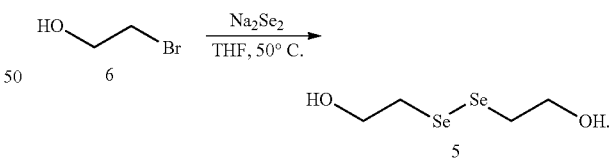

Scheme 4: Synthesis of 2,2'-diselanediylbis(ethan-1-ol), 5

Se (0.50 g, 6.33 mmol) and $NaBH_4$ (0.50 g, 13.21 mmol) were dissolved in 25 mL of $H_2O$. This vigorous reaction was stirred over 15 min. An additional 0.5 g of Se was added to ensure that all the $NaBH_4$ reacted. Excess Se was filtered off and the reddish-brown solution of $Na_2Se_2$ was transferred to a round-bottom flask. The flask was purged with $N_2$ and 0.89 mL (12.45 mmol) of 2-bromoethanol (6) in anhydrous THF was added to the $Na_2Se_2$. The reaction was run at 50° C. for 6 h, followed by liquid-liquid extraction with DCM and subsequently silica gel chromatography with 1:1 DCM: EtOAc. Low-res ESI-MS (m/z) calc for $C_4H_9Na_2O_2Se_2$ [M+2Na−H]$^+$: 294.8723, found: 294.8991. The purity of the compound was confirmed via HPLC.

Synthesis of 2.

Scheme 5: Synthesis of 10-amino-1-methoxy-3′H-spiro[benzo[c]xanthene-7,1′-isobensofuran]-3′-one, 2

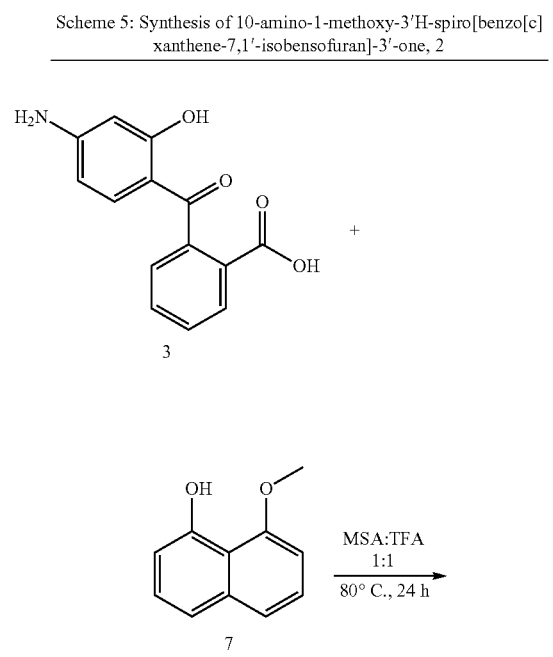

Synthesis of 1.

Scheme 6: Synthesis of 2-((2-hydroxyethyl)diselaneyl)ethyl (1-methoxy-3′-oxo-3′H-spiro[benzo[c]xanthene-7,1′-isobenzofuran]-10-yl)carbamate, 1.

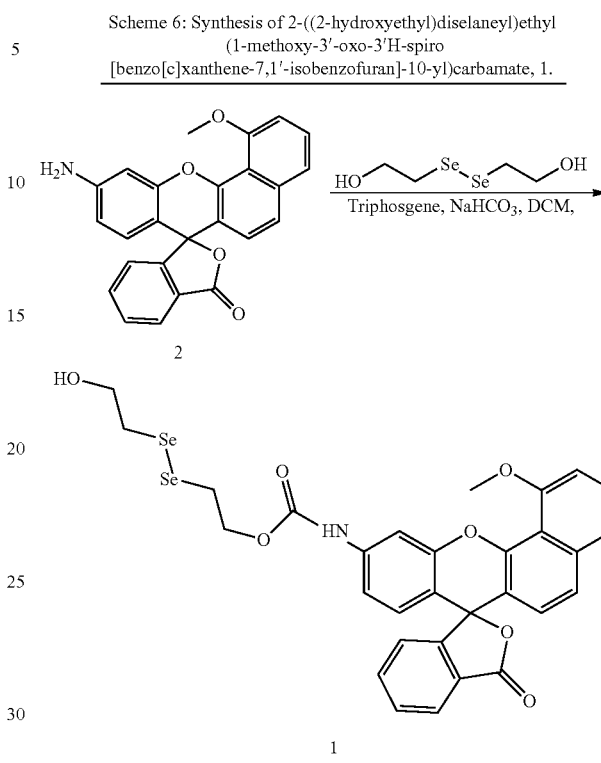

Compound 3 (150 mg, 0.58 mmol) and compound 7 (152 mg, 0.88 mmol) were dissolved in 1 mL of methanesulfonic acid, then 1 mL of TFA was added. The mixture was stirred for 16 h at 80° C. and then cooled down to rt and poured into 50 mL of DI water. The mixture was then neutralized to pH 6-7 by portion wise addition of solid NaHCO$_3$. A precipitate was formed and filtered, washed with water (25 mL), and then air dried. The compound was purified using silica gel chromatography with DCM:MeOH 9:1 as the eluent. Low-res ESI-MS (m/z) calc for $C_{25}H_{18}NO_4$ [M+H]$^+$: 396.1230, found: 396.1126. $^1$H NMR (400 MHz, DMSO-d$_6$) δ 8.03 (m, 1H), 7.79 (m, 1H), 7.74 (dd, J=7.5, 1.1 Hz, 1H), 7.57 (t, J=8.0 Hz, 1H), 7.48 (dd, J=13.3, 8.8 Hz, 2H), 7.28 (m, 1H), 7.16 (d, J=7.7 Hz, 1H), 6.42 (m, 2H), 5.76 (s, 2H), 5.69 (s, 2H), 4.06 (s, 3H). $^{13}$C NMR (101 MHz, DMSO) δ 168.83, 157.04, 153.02, 151.59, 151.31, 148.04, 136.49, 135.58, 130.04, 128.46, 128.17, 126.22, 124.58, 124.42, 124.14, 123.19, 120.30, 114.95, 112.83, 111.72, 108.26, 104.64, 99.48, 84.29, 56.42.

Compound 2 (100 mg, 252.26 µmol) was dissolved in 20 mL of DCM. Saturated aqueous NaHCO$_3$ (5 mL) was added and the biphasic mixture was cooled in an ice bath while being stirred. Triphosgene (25 mg, 84 µmol) was added to the mixture in one portion and the reaction was stirred for 15 min. The organic layer was removed, and the aqueous layer extracted with DCM (3×20 mL). Compound 5 (32 mg, 129.03 µmol) was dissolved in DCM:THF 1:1, added to the reaction mixture containing 2, and stirred overnight. Probe 1 was purified using Reverse-phase HPLC, using a C-18 column with Water:Acetonitrile gradient elution. Low-res ESI-MS (m/z) calc for $C_{30}H_{24}NO_7Se_2^-$ [M−H]$^+$: 669.9786, found: 669.9884. $^1$H NMR (400 MHz, DMSO-d$_6$) δ 10.11 (s, 1H), 8.08 (dd, 7.5, 3.1 Hz, 1H), 7.83-7.73 (m, 3H), 7.57 (t, J=8.0 Hz, 1H), 7.48 (dd, J=13.3, 8.8 Hz, 2H), 7.28 (m, 1H), 7.16 (d, J=7.7 Hz, 1H), 6.42 (m, 2H), 5.76 (s, 2H), 5.69 (s, 2H), 4.06 (s, 3H). The purity was confirmed through HPLC.

Example 2

Characterization of Probe 1

To determine if determine if probe 1 would elicit a turn-on response, dithiothreitol (DTT) was used to reduce the diselenide into the selenolate. DTT is known to reduce both disulfides and diselenides. Excitation and emission spectra were obtained for a 10 µM solution of 1 in 0.3% DMSO, 0.2% NP-40 (nonyl phenoxypolyethoxylethanol), 1 mM EDTA, and 50 mM Tris buffer, pH 7.4, initially without DTT and then with an equimolar amount of DTT (FIG. 1). An instantaneous turn-on response of the probe was observed, and the solution went from colorless to red. Maximum fluorescence was achieved promptly and the solution did not revert to the colorless form. When illumined with a long-wavelength UV lamp, the solution with DTT showed strong yellow fluorescence whereas the untreated sample showed no fluorescence (inset of FIG. 1).

To investigate the reactivity and optical responses of probe 1, an aqueous solution of 10 μM probe 1, 10 μM DTT in 0.3% DMSO, 0.2% NP-40, 1 mM EDTA and 50 mM Tris buffer, pH 7.4 was prepared. DTT is a powerful reducing agent for both diselenides and disulfides and might be expected to react with probe 1 by a mechanism similar to the TrxR1 enzyme. The solution instantly turned from colorless to red upon the addition of DTT and emitted yellow fluorescence when illuminated with UV light from a hand-held lamp. Excitation at 531 nm afforded emission with a $\lambda_{max}$ at 580 nm, as expected for the formation of compound 2, which was also monitored by HPLC-MS.

Figure 2:
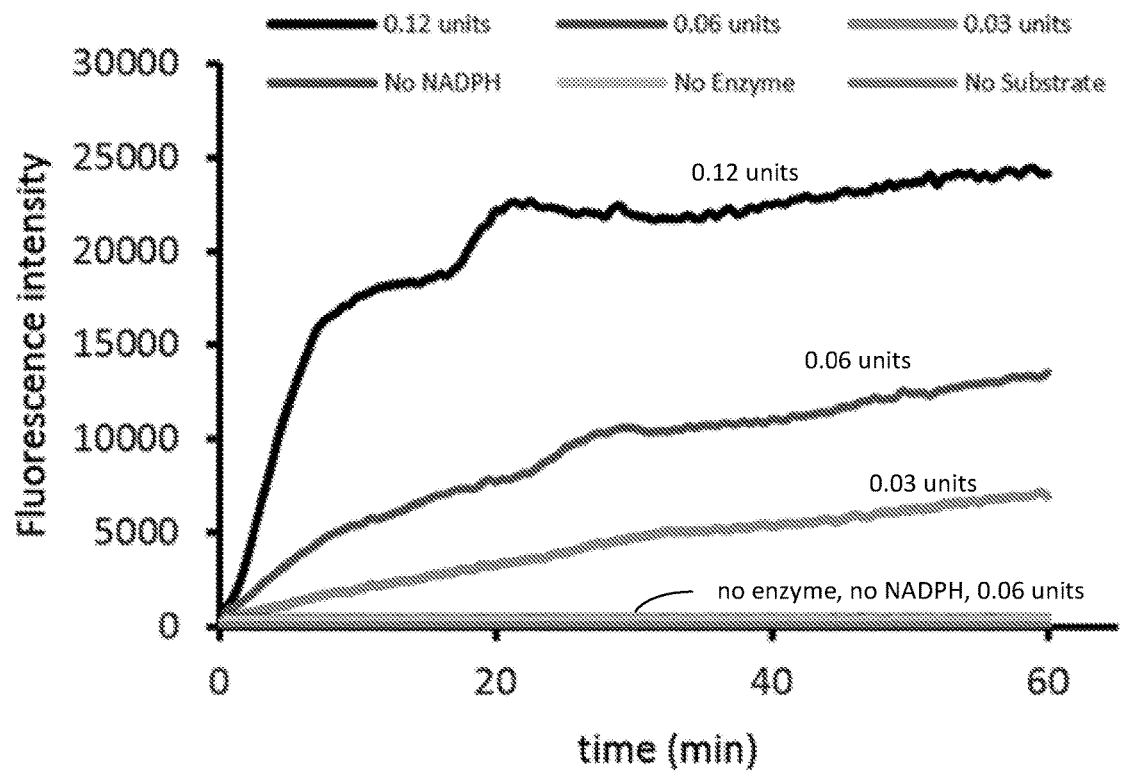
FIG. 2 is a graph of fluorescence emission versus time for an exemplary probe as disclosed herein.

Enzymatic assays were carried out using TrxR1 from rat liver in the presence of 20 μM probe 1, 10 mM EDTA, 0.2 mg/mL BSA, and 0.24 mM NADPH in phosphate buffer (100 mM, pH 7.4). This solution was pipetted into four different wells in a 96-well plate. 0.03, 0.06 and 0.12 units of TrxR1 were added to different reaction mixtures. Control experiments were set up by omitting either probe 1, NADPH or TrxR1 from the mixtures. After all the reagents had been mixed, the wells were immediately monitored for change in fluorescence ($\lambda_{ex}$=531 nm; $\lambda_{em}$=580 nm) and NADPH absorbance ($\lambda_{abs,max}$ 340 nm). TrxR1 activity was monitored via fluorescence emission increase of probe 1 ($\lambda_{ex}$=531 nm; $\lambda_{em}$=580 nm) as well as the depletion of NADPH ($\lambda_{abs}$=340 nm) upon incubation. Reactions were monitored in black 96-well plates with clear bottoms using a fluorescence plate reader. NADPH and TrxR1 were both required for the conversion of probe 1 to compound 2 and the concomitant turn-on emission (FIG. 2). As seen in FIG. 2, the fluorescence intensity increased and began to plateau at 20 min for the 0.12 units TrxR concentration. In the absence of NADPH or TrxR, no fluorescence was observed. The proposed mechanism for the reaction of probe 1 in the presence of TrxR1 and NADPH is shown in Scheme 7. Nucleophilic attack of the diselenide occurs through the TrxR1 selenocystine residue. The selenolate formed attacks the carbamate carbonyl, and an oxaselenolanone heterocycle and the fluorescent probe 2 are released.

Scheme 7

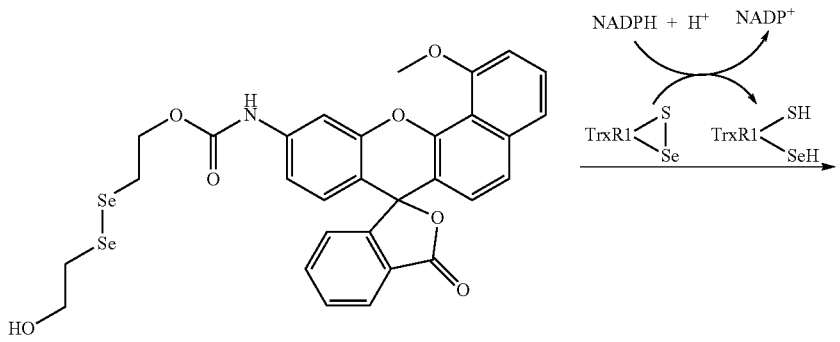

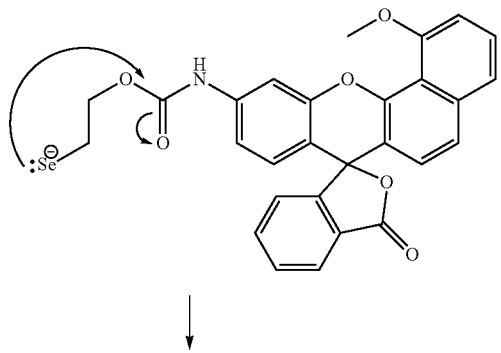

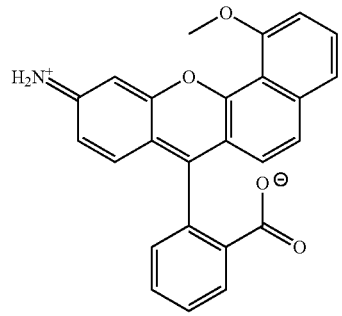
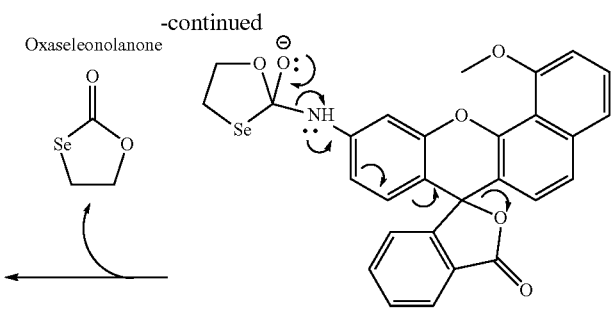

Figure 3:
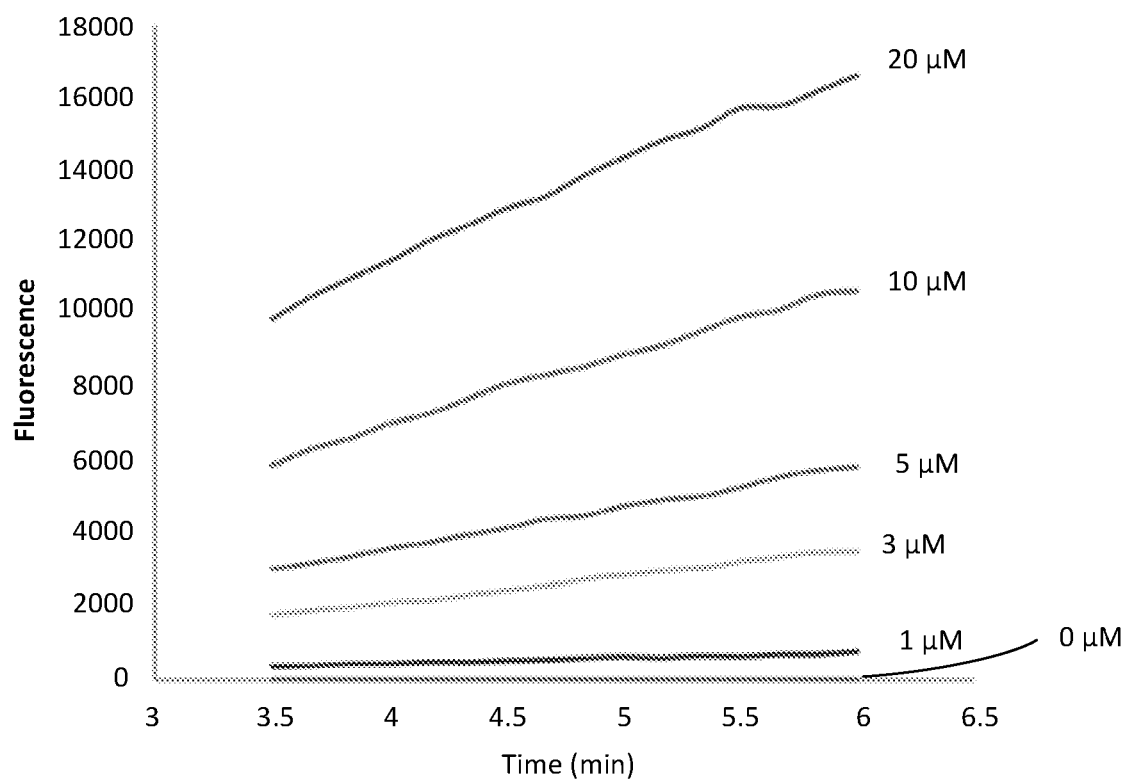
FIG. 3 is a graph of fluorescence emission versus time for varying concentrations of an exemplary probe as disclosed herein in a reaction of the probe with a thioredoxin reductase and NADPH.
Figure 4:
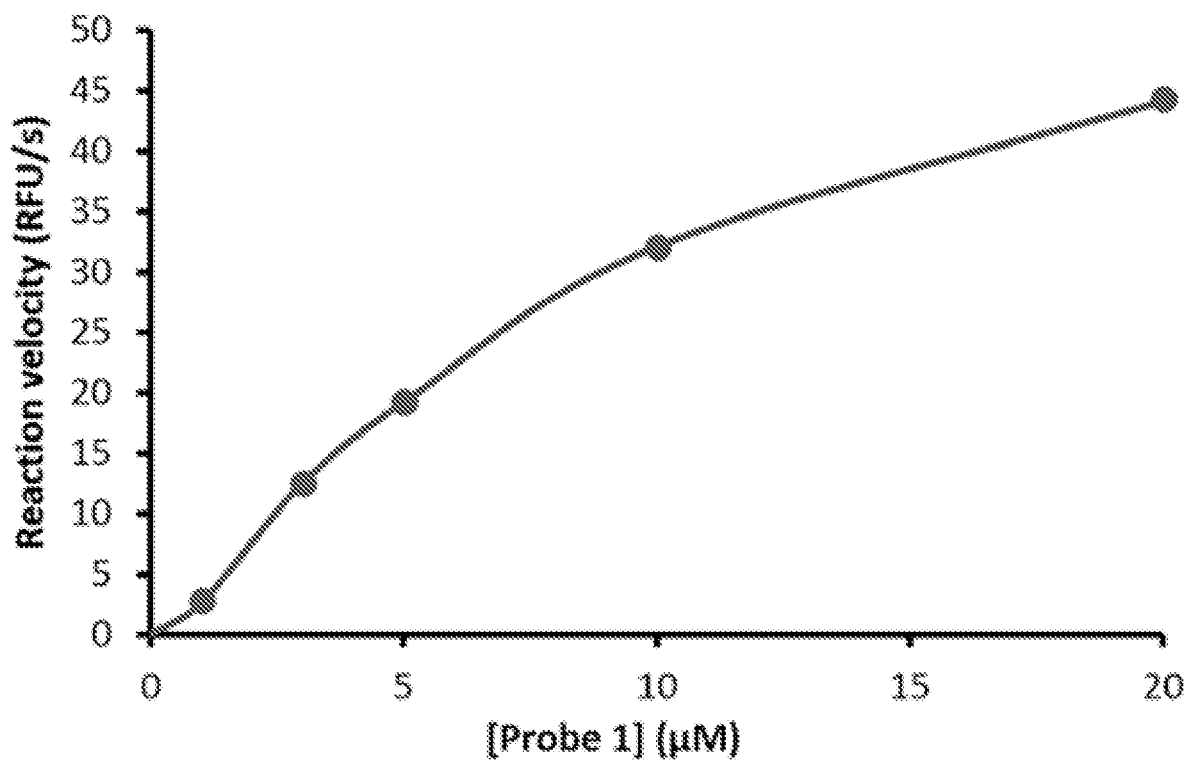
FIG. 4 is a graph of reaction rate versus substrate concentration for the exemplary probe of FIG. 3.

Kinetic studies were carried out for six reaction mixtures with varying amounts (1-20 μM) of probe 1 over 20 min. Reaction mixtures were made with concentrations of: TrxR1 0.12 units, 100 mM phosphate buffer, pH 7.4; 10 mM EDTA, 0.2 mg/mL BSA and 0.24 mM NADPH. 1 was added at different concentrations in the reaction mixture: 20 μM, 10 μM, 5 μM, 3 μM, 1 μM and 0 μM. The reaction was monitored through the change in fluorescence ($\lambda_{ex}$=531 nm; $\lambda_{em}$=580 nm) and a fluorescence vs time graph was plotted for each substrate concentration (FIG. 3). The linear portion of each graph was isolated and used in the calculation of $K_m$, which came out to be 15.89 μM. The fluorescence data also was plotted as a reaction rate vs substrate concentration graph (FIG. 4).

Figure 5:
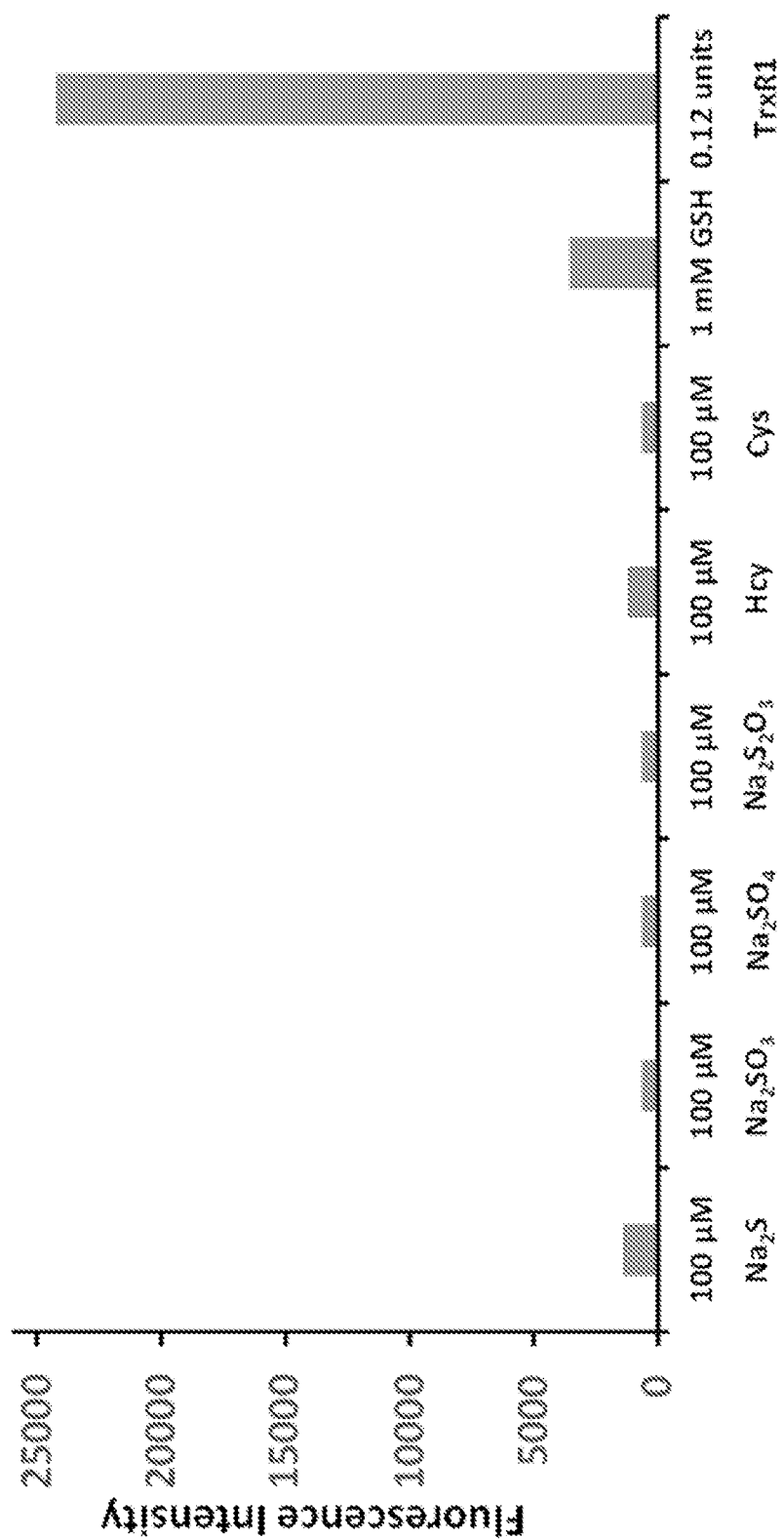
FIG. 5 is a bar graph showing fluorescence responses of an exemplary probe as disclosed herein upon incubation with TrxR1 and other potential reductants and substrates (Hcy=homocysteine, Cys=cysteine, GSH=glutathione).

The selectivity of TrxR1 for probe 1 was evaluated against other biological thiols and ions. Probe 1, at a concentration of 20 μM, was incubated for 20 minutes with 0.12 units TrxR1, 100 μM $Na_2S$, 100 μM $Na_2SO_3$, 100 μM $Na_2SO_4$, 100 μM $Na_2S_2O_3$, 100 μM homocysteine (Hcy), 100 μM cysteine (Cys), or 1 mM glutathione (GSH) in 100 mM phosphate buffer, pH 7.4; 10 mM EDTA, 0.2 mg/mL BSA and 0.24 mM NADPH. None afforded a significant change in fluorescence comparable to that of TrxR1 (FIG. 5).

TrxR1 was shown to be selective for probe 1 with minimal interference from other reductive biological species. The selectivity is attributed to the nucleophilicity of the selenocysteine residue on the active site of TrxRs. This study shows the potential of probe 1 as a useful targeting tool for TrxRs and in the imaging of cutaneous melanoma in which the cytosolic form of the enzyme is overexpressed.

MTS cytotoxicity assays for probe 1 were carried out using the CellTiter 96® Aqueous One Solution Cell Proliferation Assay (Promega Corporation, Madison, WI), with A375 and SK-MEL-5 melanoma cell lines. The following treatment groups were made:

| A375 | SK-MEL-5 |
|---|---|
| Treatment Groups: | Treatment Groups: |
| Media only | Media only |
| 0.1% DMSO | 0.1% DMSO |
| Probe 1: | Probe 1: |
| 1, 3, 5, 7, 10, 30 μM | 0.3, 1, 1.5, 2.25, 3, 10 μM |
| Recovery: | Recovery: |
| 24, 48, 72 hrs | 24, 48, 72 hrs |

$IC_{50}$ values for probe 1 with A375 cells were determined to be 3.527, 2.233, and 2.552 μM at 24, 48, and 72 hours, respectively. For SK-MEL-5 cells, the $IC_{50}$ values were 4.770, 3.097, and 2.299 μM at 24, 48, and 72 hours, respectively. The $IC_{50}$ is the probe concentration required to kill 50% of the cells in the specified time period.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound according to Formula I, or an ionized form or salt thereof:

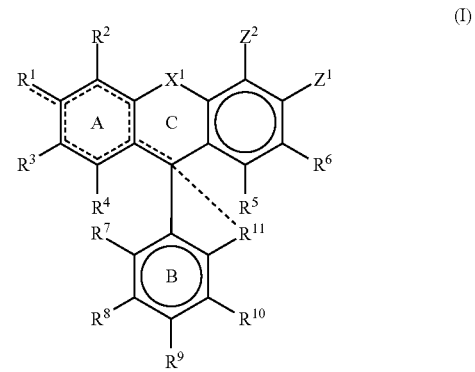

where each bond depicted as "-----" is a single or double bond as needed to satisfy valence requirements;

$Z^1$ and $Z^2$ independently are hydrogen, hydroxyl, or thiol, or $Z^1$ and $Z^2$ together with the atoms to which they are attached form a substituted or unsubstituted 6-membered ring;

$X^1$ is O, S, Se, $Si(R^a)(R^b)$, $Ge(R^a)(R^b)$, $Sn(R^a)(R^b)_2$, $C(R^a)(R^b)_2$, or $NR^b$ where $R^a$ is H or $C_1$-$C_{10}$ alkyl and $R^b$ is H, $C_1$-$C_{10}$ alkyl, —COOH, or —COOR$^c$ where $R^c$ is $C_1$-$C_{10}$ alkyl or a conjugatable moiety;

$R^1$ is hydrogen, hydroxyl, halogen, thiol, amino, alkyl amino, oxygen, sulfur, imino, iminium, alkyl imino, alkyl iminium, cycloalkyl imino, or a diselenide moiety, and $R^2$ and $R^3$ independently are hydrogen, hydroxy, thiol, $C_1$-$C_{10}$ alkyl, carboxyalkyl, amino, alkoxy, or halogen, or $R^1$-$R^3$ together with Ring A form a tricyclic ring system with a nitrogen at $R^1$ and a single bond between $R^1$ and ring A;

$R^4$-$R^6$ independently are hydrogen, hydroxy, thiol, $C_1$-$C_{10}$ alkyl, carboxyalkyl, amino, alkoxy, or halogen;

$R^7$, $R^8$, and $R^{10}$ independently are hydrogen, alkyl, acyl, carboxyl, nitro, amino, alkyl amino, —$SO_3H$, —COOH, or —COOR$^d$ where $R^d$ is $C_1$-$C_{10}$ alkyl or a conjugatable moiety;

$R^9$ is hydrogen, alkyl, acyl, carboxyl, nitro, amino, alkyl amino, —$SO_3H$, a diselenide moiety, —COOH, or —COOR$^d$ where $R^d$ is $C_1$-$C_{10}$ alkyl or a conjugatable moiety; and $R^{11}$ is one or more atoms forming a ring system with rings C and B and the bond depicted as "=====" in ring C is a single bond, or $R^{11}$ is —COOH, —COO$^-$ or —COOR$^e$ where $R^e$ is $C_1$-$C_{10}$ alkyl or a counter ion with a net single positive charge and the bond depicted as "=====" in ring C is a double bond, wherein the compound comprises at least one diselenide moiety, and each diselenide moiety independently has a formula —Y—C(Q)O—(CH$_2$)$_m$—Se—Se—(CH$_2$)$_n$—OR$^f$, where R$^f$ is hydrogen or $C_1$-$C_3$alkyl, Q is O or S, Y is O or N(R$^g$) where R$^g$ is H or alkyl, and m and n independently are integers from 1-5.

2. The compound of claim 1 where $Z^1$ and $Z^2$ together with the atoms to which they are attached form a substituted or unsubstituted 6-membered ring and the compound has a structure according to Formula II, or an ionized form or salt thereof:

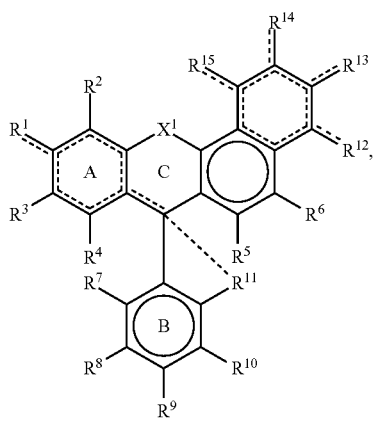

(II)

wherein $R^{12}$-$R^{14}$ independently are hydrogen, halogen, hydroxy, oxygen, thiol, amino, alkyl amino, alkoxy, sulfur, imino, iminium, alkyl imino, or alkyl iminium; and $R^{15}$ is hydrogen, halogen, hydroxy, oxygen, thiol, amino, alkyl amino, alkoxy, sulfur, imino, iminium, alkyl imino, or alkyl iminium, or a diselenide moiety.

3. The compound of claim 1 where $X^1$ is O, Se, Si(R$^a$)(R$^b$), or NR$^b$.

4. The compound of claim 1 where:

$R^{11}$ is —COO— and forms a lactone ring; or $R^{11}$ is —COOH, —COO$^-$ or —COOR$^e$ where R$^e$ is a counter ion with a net single positive charge.

5. The compound of claim 1 where:

(i) $R^2$-$R^4$ are hydrogen; or (ii) $R^5$ and $R^6$ are hydrogen; or (iii) $R^7$ and $R^{10}$ are hydrogen; or (iv) $R^8$ and $R^9$ independently are hydrogen or —COOR$^d$, or (v) $R^{12}$-$R^{14}$ are hydrogen; or (vi) any combination of (i), (ii), (iii), (iv) and (v).

6. The compound of claim 2 where:

(i) $R^1$ is —Y—C(Q)O—(CH$_2$)$_m$—Se—Se—(CH$_2$)$_n$—OR$^f$, and $R^{15}$ is $C_1$-$C_3$ alkoxy or hydroxy; or (ii) $R^1$ is O or alkyl iminium, and $R^{15}$ is —Y—C(Q)O—(CH$_2$)$_m$—Se—Se—(CH$_2$)$_n$—OR$^f$; or (iii) both $R^1$ and $R^{15}$ independently are —Y—C(Q)O—(CH$_2$)$_m$—Se—Se—(CH$_2$)$_n$—OR$^f$.

7. The compound of claim 1 where:

$Z^1$ is hydroxyl or thiol;

$Z^2$ is hydrogen;

$R^1$ is hydroxyl or thiol; and $R^9$ is —Y—C(Q)O—(CH$_2$)$_m$—Se—Se—(CH$_2$)$_n$—OR$^f$.

8. The compound of claim 1 where:

(i) m is 2; or (ii) n is 2; or (iii) R$^f$ is H; or (iv) Y is O or N(H); or (v) any combination of (i), (ii), (iii), and (iv).

9. The compound of claim 1 where the compound is

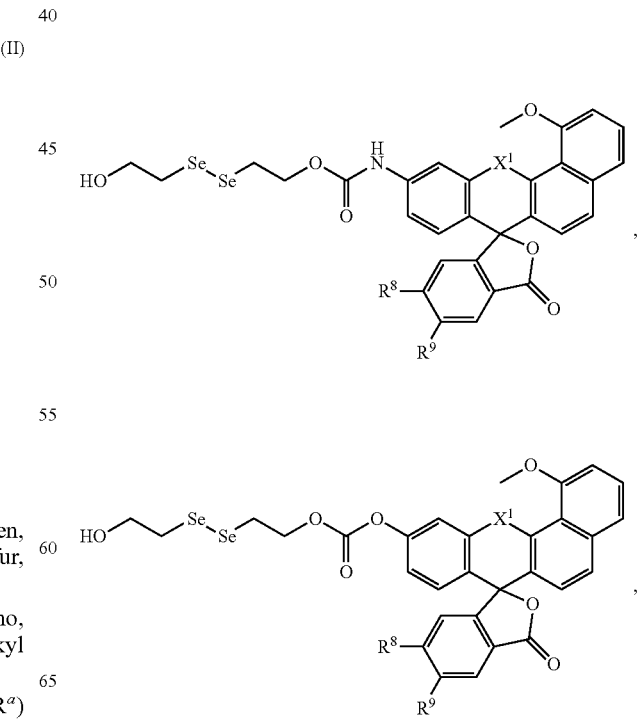

41
-continued
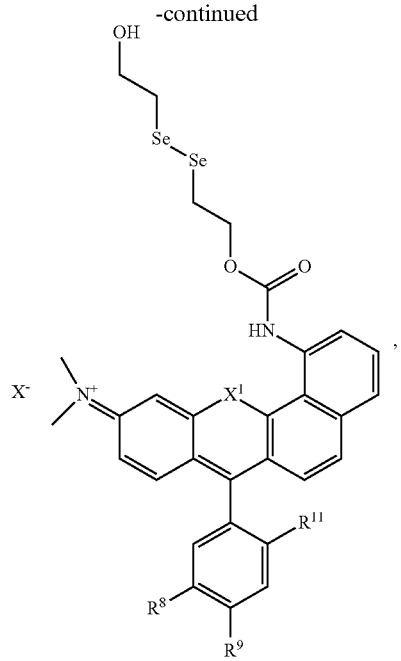
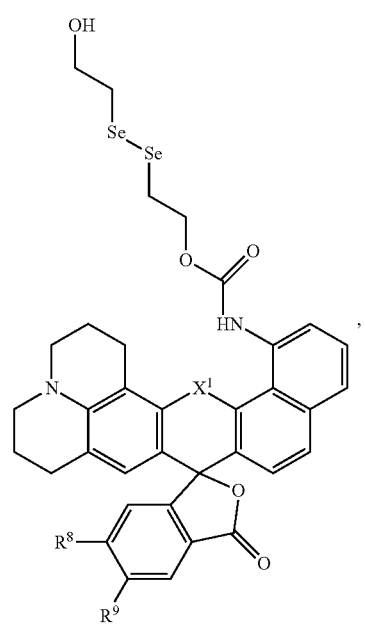
42
-continued
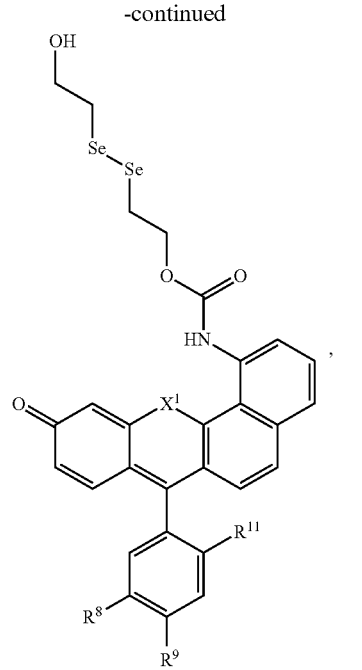
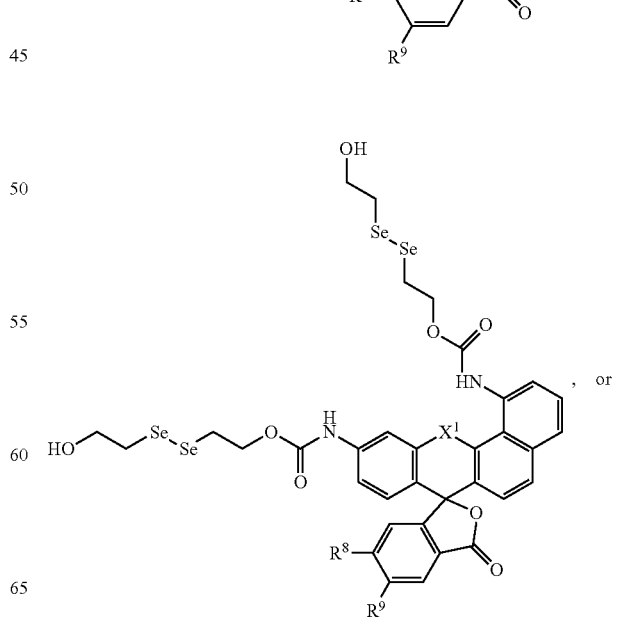

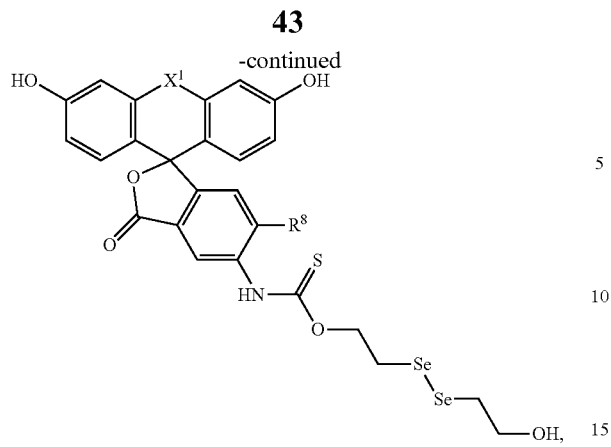

where $X^1$ is O, Se, or Si($R^a$)($R^b$);
$X^-$ is absent or a counter ion with a net single negative charge;
$R^8$ and $R^9$ independently are hydrogen, alkyl, acyl, carboxyl, nitro, amino, alkyl amino, —SO$_3$H, —COOH, or —COOR$^d$ where $R^d$ is C$_1$-C$_{10}$ alkyl or a conjugatable moiety; and
$R^{11}$ is —COOH, —COO$^-$, or —COOR$^e$ where $R^e$ is a counter ion with a net single positive charge.

10. The compound of claim 1 where the compound is

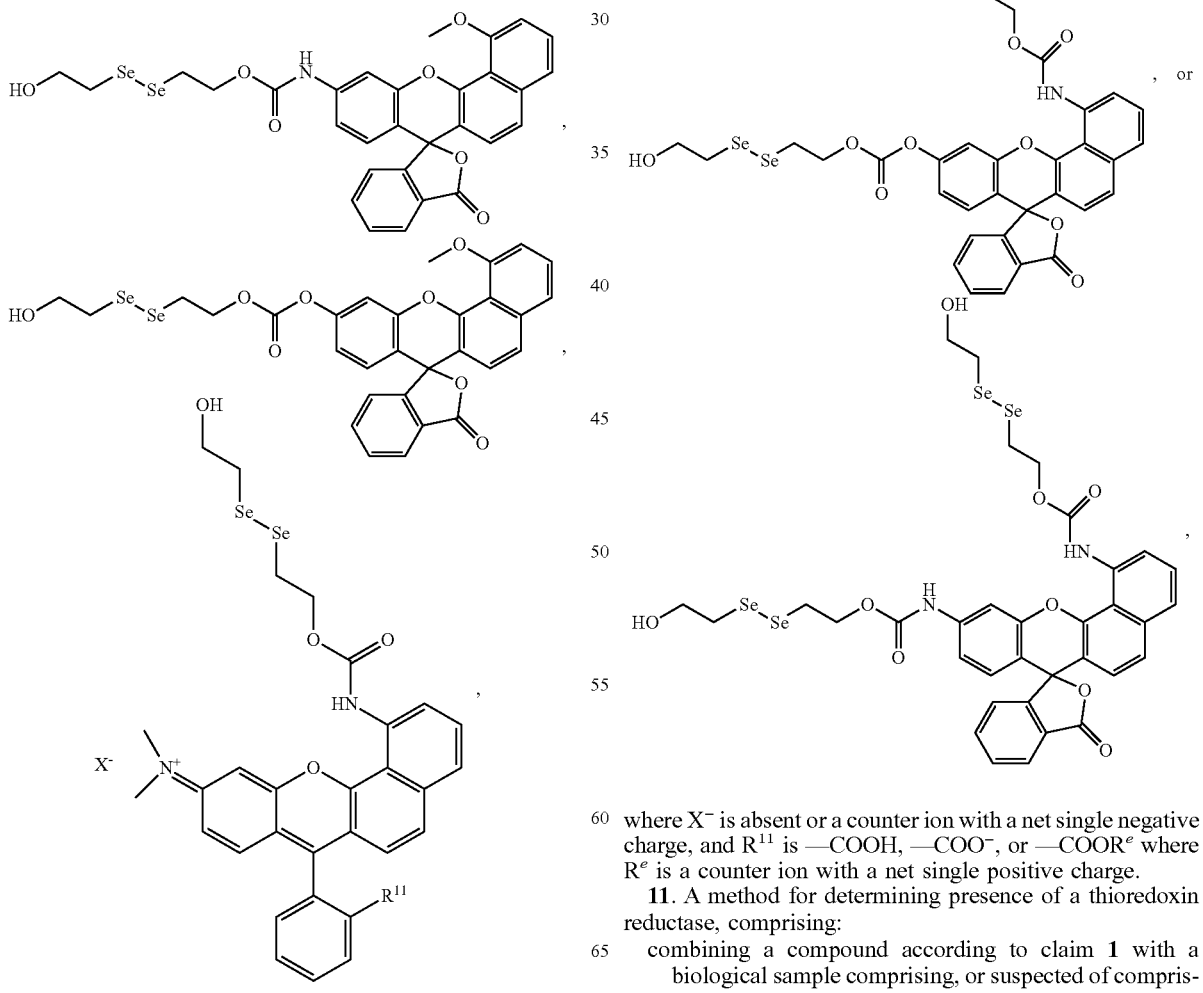

where $X^-$ is absent or a counter ion with a net single negative charge, and $R^{11}$ is —COOH, —COO$^-$, or —COOR$^e$ where $R^e$ is a counter ion with a net single positive charge.

11. A method for determining presence of a thioredoxin reductase, comprising:
combining a compound according to claim 1 with a biological sample comprising, or suspected of comprising, a thioredoxin reductase;

allowing a reaction between the biological sample and the compound to proceed for an effective period of time to produce a detectable change in the compound's color or emission spectrum, where the detectable change indicates that the thioredoxin reductase is present in the biological sample; and detecting the change.

12. The method of claim 11 where:
(i) the thioredoxin reductase comprises TrxR1; or
(ii) the effective time is 1-60 minutes; or
(iii) detecting the change comprises detecting an increase in fluorescence intensity at a wavelength within a range of 570-590 nm after the effective period of time; or
(iv) any combination of (i), (ii), and (iii).

13. The method of claim 11 where the effective time is sufficient for the thioredoxin reductase to cleave the diselenide moiety or diselenide moieties from at least some molecules of the compound, thereby producing a seminaphthofluorophore.

14. The method of claim 13 where the seminaphthofluorophore has a fluorescence emission maximum at a wavelength within a range of 550-800 nm.

15. The method of claim 11 where the biological sample comprises a tissue sample.

16. The method of claim 15 where the biological sample includes cancer cells or neurological tissue.

17. The method of claim 16 where the cancer cells comprise melanoma cells, lung carcinoma cells, or prostate cancer cells.

18. The method of claim 15 where combining the compound with the biological sample comprises combining the tissue sample and a solution comprising the compound, phosphate-buffered saline pH 7.0-7.5, and DMSO.

19. The method of claim 11, wherein combining the compound with the biological sample is performed in vivo.

20. A method for determining presence of a thioredoxin reductase, comprising: providing a compound selected from

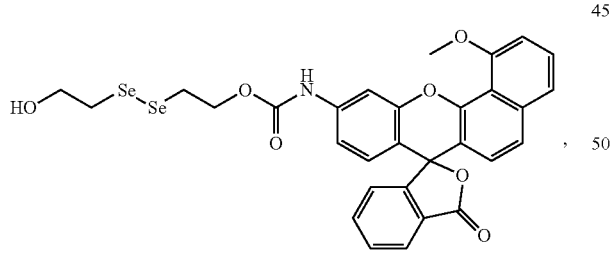

,

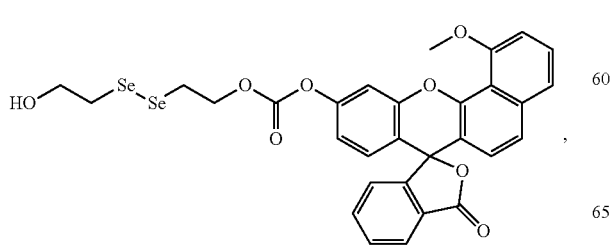

,

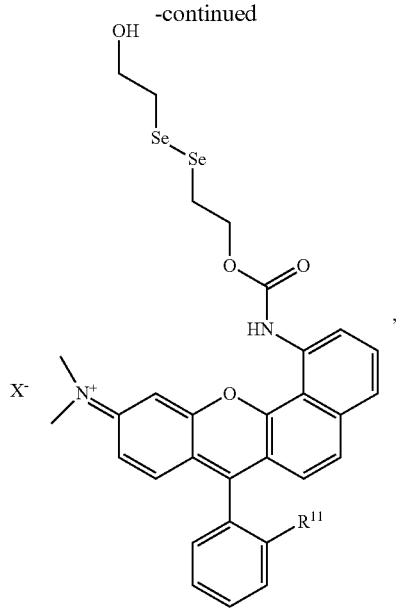

,

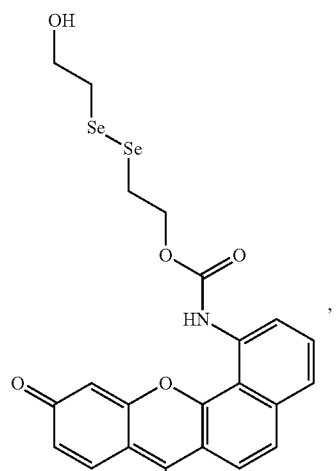

,

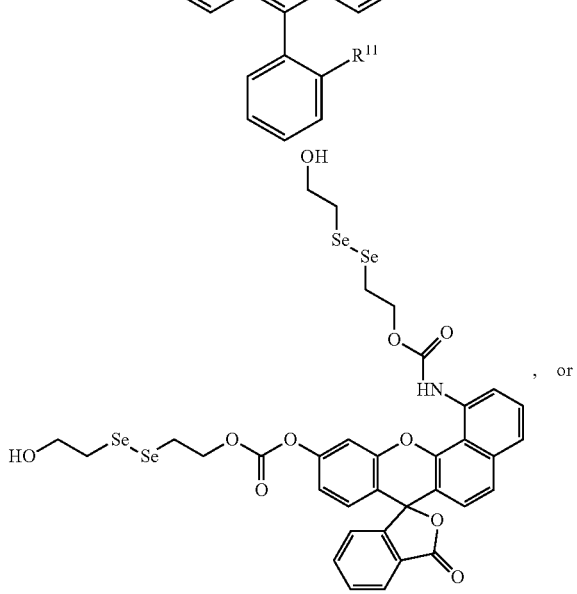

, or

-continued

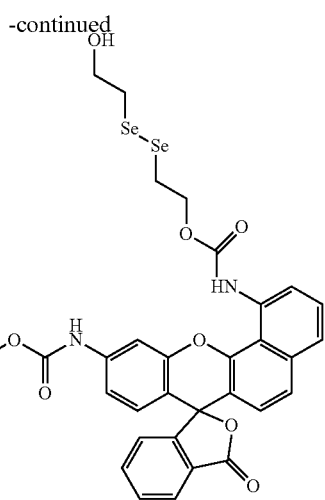

where X⁻ is absent or a counter ion with a net single negative charge, and $R^{11}$ is —COOH, —COO⁻, or —COOR$^e$ where R$^e$ is a counter ion with a net single positive charge;

combining the compound with a biological sample;

allowing a reaction between the biological sample and the compound to proceed for an effective period of time of from 1 to 60 minutes to produce a seminaphthofluorophore having a fluorescence emission maximum at a wavelength within a range of 550-800 nm if thioredoxin reductase is present in the biological sample; and analyzing the solution by visual inspection, spectrophotometry, or emission spectroscopy after the effective period of time to detect a color change or an increase in fluorescence intensity at a wavelength within a range of 570-590 nm if thioredoxin reductase is present in the biological sample.

* * * * *